US008420788B2

(12) United States Patent
Jirsrtöm et al.

(10) Patent No.: US 8,420,788 B2
(45) Date of Patent: Apr. 16, 2013

(54) EPITOPES DERIVED FROM SATB2 AND USES THEREOF

(75) Inventors: Karin Jirsrtöm, Limhamn (SE); Fredrik Pontén, Uppsala (SE); Mathias Uhlén, Stocksund (SE)

(73) Assignee: Atlas Antibodies AB, Stockholm (SE)

( * ) Notice: Subject to any disclaimer, the term of this patent is extended or adjusted under 35 U.S.C. 154(b) by 6 days.

(21) Appl. No.: 13/062,820

(22) PCT Filed: Oct. 6, 2009

(86) PCT No.: PCT/EP2009/062956
§ 371 (c)(1), (2), (4) Date: May 10, 2011

(87) PCT Pub. No.: WO2010/040737
PCT Pub. Date: Apr. 15, 2010

(65) Prior Publication Data
US 2011/0218379 A1  Sep. 8, 2011

Related U.S. Application Data

(60) Provisional application No. 61/102,948, filed on Oct. 6, 2008.

(30) Foreign Application Priority Data

Oct. 6, 2008 (EP) ..................................... 08165897

(51) Int. Cl.
*C07K 16/00* (2006.01)
(52) U.S. Cl.
USPC ....................................... 530/391.1; 436/547
(58) Field of Classification Search .................. None
See application file for complete search history.

(56) References Cited

U.S. PATENT DOCUMENTS

| | | | |
|---|---|---|---|
| 2003/0129207 A1 | 7/2003 | Meagher et al. | |
| 2007/0061916 A1* | 3/2007 | Kovalic et al. | 800/278 |
| 2008/0311567 A1 | 12/2008 | Bruckl et al. | |
| 2009/0220975 A1* | 9/2009 | Uhlen et al. | 435/6 |
| 2009/0270267 A1 | 10/2009 | Akiyama et al. | |

FOREIGN PATENT DOCUMENTS

| | | |
|---|---|---|
| EP | 1862803 A1 | 12/2007 |
| GB | 2435882 A | 9/2007 |
| WO | WO 00/40752 A2 | 7/2000 |
| WO | WO0175067 | * 10/2001 |
| WO | WO 03/022126 A2 | 3/2003 |
| WO | WO 2005/107396 A2 | 11/2005 |
| WO | WO 2006/015742 A2 | 2/2006 |

OTHER PUBLICATIONS

EPO Extended European Search Report, Appl. No. 08165897.3, Mar. 10, 2009, pp. 1-6.

PCT International Preliminary Report on Patentability and Written Opinion of the International Searching Authority, Appl. No. PCT/EP2009/062956, Apr. 12, 2011, pp. 1-6.
Rockberg, J. et al, "Epitope mapping of antibodies using bacterial surface display," Nature Methods, Dec. 2008, vol. 5, No. 12, pp. 1039-1045.
Agaton et al., "Genome-based proteomics", Electrophoresis, vol. 25, 2004, pp. 1280-1288.
Andersson et al., "Analysis of Protien Expression in Cell Microarrays: A Tool for Antibody-based Proteomics", Journal of Histochemistry & Cytochemistry, vol. 54, No. 12, 2006, pp. 1413-1423.
Australian Office Action dated Jan. 20, 2011, for Application No. 2007256391.
Bode et al., "Transcriptional Augmentation: Modulation of Gene Expression by Scaffold/Matrix Attached Regions (S/MAR Elements)", Crit Rev Eukaryot Gene Expr., vol. 10, No. 1, 2000, 26 pages.
Britanova et al., "Novel transcription factor Satb2 interacts with matrix attachment region DNA elements in a tissue-specific manner and demonstrates cell-type-dependent expression in the developing mouse CNS", European Journal of Neuroscience, vol. 21, 2005, pp. 658-668.
Cheng et al., "The clinical implications of MMP-11 and CK-20 expression in human breast cancer", Clinica Chimica Acta, vol. 411, 2010, pp. 234-241 (Available online Nov. 13, 2009).
Chung et al., "SATB2 augments ΔNp63α in head and neck squamous cell carcinoma", EMBO reports, Published Online Sep. 10, 2010, p. 1-7.
Dickinson et al., "A Tissue-Specific MAR/SAR DNA-Binding Protein with Unusual Binding Site Recognition", Cell, vol. 70, Aug. 21, 1992, pp. 631-645.
Dobreva et al., "SUMO modification of a novel MAR-binding protein, SATB2, modulates immunoglobulin μ gene expression", Genes & Developement, vol. 17, 2003, pp. 3048-3061.
European Office Action dated Mar. 1, 2010, for Application No. 07725799.6.
Extended European Search Report dated Jun. 25, 2010, for Application No. 10158956.2.
Fitzpatrick et al., "Identification of SATB2 as the cleft palate gene on 2q32-q33", Human Molecular Genetics, vol. 12, No. 19, 2003, pp. 2491-2501.
Giribaldi et al., "Specific Detection of Cytokeratin 20-Positive Cells in Blood of Colorectal and Breast Cancer Patients by a High Sensitivity Real-Time Reverse Transcriptase-Polymerase Chain Reaction Method", Journal of Molecular Diagnostics, vol. 8, No. 1, Feb. 2006, pp. 105-112.

(Continued)

*Primary Examiner* — Lei Yao
(74) *Attorney, Agent, or Firm* — Birch, Stewart, Kolasch & Birch, LLP

(57) ABSTRACT

The present invention relates to an affinity ligand capable of selective interaction with an epitope sequence consisting of 47 amino acids or less and comprising the amino acid sequence of SEQ ID NO:1 and/or SEQ ID NO:2. Further, it relates to a polypeptide consisting of the epitope sequence and to uses of the affinity ligand and the polypeptide.

7 Claims, 7 Drawing Sheets

OTHER PUBLICATIONS

Groene et al., "Transcriptional census of 36 microdissected colorectal cancers yields a gene signature to distinguish UICC II and III", International Journal of Cancer, vol. 119, 2006, pp. 1829-1836 (Published online May 23, 2006).

Kampf et al., "Antibody-Based Tissue Profiling As a Tool for Clinical Proteomics", Clinical Proteomics Journal, vol. 1, 2004, pp. 285-299.

Kikuno et al., "Prediction of the Coding Sequences of Unidentified Human Genes. XIV. The Complete Sequences of 100 New cDNA Clones from Brain Which Code for Large Proteins in vitro", DNA Research, vol. 6, 1999, pp. 197-205.

Kummar et al., "Cytokeratin 7 and 20 staining for the diagnosis of lung and colorectal adenocarcinoma", British Journal of Cancer. vol. 86, 2002, pp. 1884-1887.

Lindskog et al., "Selection of protein epitopes for antibody production", BioTechniques, vol. 38, No. 5, May 2005, pp. 723-727.

Pasche et al., "Molecular markers in prognosis of colorectal cancer and prediction of response to treatment", Best Practice & Research Clinical Gastroenterology, vol. 16, No. 2, 2002, pp. 331-345, XP-002447570.

Patani et al., "The mRNA expression of SATB1 and SATB2 in human breast cancer", Cancer Cell International, vol. 9, No. 18, Jul. 30, 2009, 10 pages.

Salahshor et al., "Differential gene expression profile reveals deregulation of pregnancy specific β1 glycoprotein 9 early during colorectal carcinogenesis", BMC Cancer, vol. 5, No. 66, Jun. 27, 2005, 14 pages.

Soong et al., "Quantitative Reverse Transcription-Polymerase Chain Reaction Detection of Cytokeratin 20 in Noncolorectal Lymph Nodes", Clinical Cancer Research, vol. 7, Nov. 2001, pp. 3423-3429.

TOT, "Cytokeratins 20 and 7 as biomarkers: usefulness in discriminating primary from metastatic adenocarcinoma," European Journal of Cancer, vol. 38, 2002, pp. 758-763.

U.S. Office Action dated Apr. 5, 2011, for U.S. Appl. No. 12/302,248.

U.S. Office Action dated Jul. 22, 2010, for U.S. Appl. No. 12/302,248.

U.S. Office Action dated Oct. 12, 2010, for U.S. Appl. No. 12/302,248.

Uhlen et al., "A Human Protein Atlas for Normal and Cancer Tissues Based on Antibody Proteomics", Molecular & Cellular Proteomics, vol. 4, No. 12, Aug. 27, 2005, pp. 1920-1932.

Uhlen et al., "Antibody-based Proteomics for Human Tissue Profiling", Molecular & Cellular Proteomics vol. 4, No. 4, 2005, pp. 384-393.

Van Buggenhout et al., "The del(2)(q32.2q33) deletion syndrome defined by clinical and molecular characterization of four patients", European Journal of Medical Genetics, vol. 48, 2005, pp. 276-289 (Available Online Jun. 6, 2005).

Wang et al., "Down-regulated expression of SATB2 is associated with the metastasis and poor prognosis in colorectal cancer", Journal of Pathology, vol. 219, 2009, pp. 114-122 (Published online May 8, 2009).

Yasui et al., "SATB1 targets chromatin remodelling to regulate genes over long distances", Nature, vol. 419, Oct. 10, 2002, pp. 641-645.

* cited by examiner

| Count | | 5E2_NFdic | | |
|---|---|---|---|---|
| | | <2 % positive cells | ≥ 2% positive cells | Total |
| 8F11_NFdic | 0-75% | 8 | 12 | 20 |
| | >75% | 13 | 238 | 251 |
| Total | | 21 | 250 | 271 |

EPITOPES DERIVED FROM SATB2 AND USES THEREOF

This application is the National Phase of PCT/EP2009/062956 filed on Oct. 6, 2009, which claims priority under 35 U.S.C. 119(e) to U.S. Provisional Application No. 61/102,948 filed on Oct. 6, 2008 and under 35 U.S.C. 119(a) to patent application Ser. No. 08165897.3 filed in the European Patent Office on Oct. 6, 2008, all of which are hereby expressly incorporated by reference into the present application.

TECHNICAL FIELD

The present disclosure relates to the field of epitopes and affinity ligands binding thereto. Further, some aspects of the present disclosure relates to methods employing the affinity ligands, e.g., for colorectal cancer prognostics.

BACKGROUND

Cancer

Cancer is one of the most common causes of disease and death in the western world. In general, incidence rates increase with age for most forms of cancer. As human populations continue to live longer, due to an increase of the general health status, cancer will affect an increasing number of individuals. The cause of most common cancer types is still at large unknown, although there is an increasing body of knowledge providing a link between environmental factors (diet, tobacco smoke, UV radiation etc) as well as genetic factors (germ line mutations in "cancer genes" such as p53, APC, BRCA1, XP etc) and the risk for development of cancer.

No definition of cancer is entirely satisfactory from a cell biological point of view, despite the fact that cancer is essentially a cellular disease and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events that ultimately lead to growth of a malignant tumor. This multi-step process includes several rate-limiting steps, such as addition of mutations and possibly also epigenetic events, leading to formation of cancer following stages of precancerous proliferation. The stepwise changes involve accumulation of errors (mutations) in vital regulatory pathways that determine cell division, asocial behavior and cell death. Each of these changes may provide a selective Darwinian growth advantage compared to surrounding cells, resulting in a net growth of the tumor cell population. It is important to emphasize that a malignant tumor does not only consist of the transformed tumor cells themselves but also surrounding normal cells which act as a supportive stroma. This recruited cancer stroma consists of connective tissue, blood vessels and various other normal cells, e.g. inflammatory cells, which act in concert to supply the transformed tumor cells with signals necessary for continued tumor growth.

The most common forms of cancer arise in somatic cells and are predominantly of epithelial origin, e.g. prostate, breast, colon, urothelial and skin, followed by cancers originating from the hematopoetic lineage, e.g. leukemia and lymphoma, neuroectoderm, e.g. malignant gliomas, and soft tissue tumors, e.g. sarcomas.

Cancer Diagnostics and Prognostics

Microscopic evaluation of a tissue section taken from a tumor remains the golden standard for determining a diagnosis of cancer. For microscopic diagnosis, biopsy material from suspected tumors is collected and examined under the microscope. To obtain a firm diagnosis, the tumor tissue is fixated in formalin, histo-processed and paraffin embedded. From the resulting paraffin block, tissue sections can be produced and stained using both histochemical, i.e. hematoxylin-eosin staining, and immunohistochemical methods. The surgical specimen is then evaluated with pathology techniques, including gross and microscopic analysis. This analysis forms the basis for assigning a specific diagnosis, i.e. classifying the tumor type and grading the degree of malignancy, of a tumor.

Malignant tumors can be categorized into several stages according to classification schemes specific for each cancer type. The most common classification system for solid tumors is the tumor-node-metastasis (TNM) staging system. The T stage describes the local extent of the primary tumor, i.e. how far the tumor has invaded and imposed growth into surrounding normal tissues, whereas the N stage and M stage describe how the tumor has developed into metastasis, with the N stage describing spread of tumor to lymph nodes and the M stage describing growth of tumor in other distant organs. Early stages include: T0-1, N0, M0, representing localized tumors with negative lymph nodes. More advanced stages include: T1-4, N0-4, M0, localized tumors with more widespread growth and T1-4, N1-4, M0, tumors that have metastasized to lymph nodes and T1-4, N1-4, M1, tumors with a metastasis detected in a distant organ. Staging of tumors is often based on several forms of examinations, including surgical, radiological and histopathological analyses. In addition to the staging, there is also a classification system to grade the level of malignancy for most tumor types. The grading systems rely on morphological assessment of a tumor tissue sample and are based on the microscopic features found in a given tumor. These grading systems may be based on the degree of differentiation, proliferation and atypical appearance of the tumor cells. Examples of generally employed grading systems include Gleason grading for prostatic carcinomas and Elston-Ellis grading for breast carcinomas.

Accurate staging and grading is crucial for a correct diagnosis and provides an instrument to predict a prognosis. The diagnostic and prognostic information for a specific tumor subsequently determines an adequate therapeutic strategy for a given cancer patient. The most commonly used method, in addition to histochemical staining of tissue sections, to obtain more information regarding a tumor is immunohistochemical staining (IHC). IHC allows for the detection of protein expression patterns in tissues and cells using specific antibodies. The use of IHC in clinical diagnostics allows for the detection of immunoreactivity in different cell populations, in addition to the information regarding tissue architecture and cellular morphology that is assessed from the histochemically stained tumor tissue section. IHC can be important to support the accurate diagnosis, including staging and grading, of a primary tumor as well as in the diagnostics of metastases of unknown origin. The most commonly used antibodies in clinical practice today include antibodies against cell type "specific" proteins, e.g. PSA (prostate), MelanA (melanocytes), Thyroglobulin (thyroid gland) and antibodies recognizing intermediate filaments (epithelial, mesenchymal, glial) cluster of differentiation (CD) antigens (hematopoetic, sub-classification of lymphoid cells) and markers of malignant potential, e.g. Ki67 (proliferation), p53 (commonly mutated tumor suppressor gene) and HER-2 (growth factor receptor).

Aside from IHC, the use of in situ hybridization for detecting gene amplification and gene sequencing for mutation analysis are evolving technologies within cancer diagnostics. In addition, global analysis of transcripts, proteins or metabolites all add important information. However, most of these analyses still represent basic research and have yet to be evaluated and standardized for the use in clinical medicine.

Adenocarcinomas from Colon and Rectum (Colorectal Cancer)

Colorectal cancer, a malignant epithelial tumor that presents as an adenocarcinoma, is one of the most common forms of human cancer worldwide. Data from the GLOBOCAN 2002 database presented by Parkin et al show that around 1 million new cases of colorectal cancer are identified yearly (Parkin D M et al (2005) CA Cancer J Clin 55, 74-108). Further, the incidence of colorectal cancer in the world is approximately 9.4% of all cancers, and colorectal cancer constitutes the second most common cause of death in the western world. The five-year survival rate of colorectal cancer is approximately 60% in the western world but as low as 30% in Eastern Europe and India.

Early detection and surgery with excision of the tumor is currently of critical importance for a successful treatment. For localized tumors, i.e. tumors that have not evolved into a metastasizing disease, surgical intervention with radical resection of the tumor and surrounding bowel and tissues is performed. Colorectal tumors are categorized into several stages according to Dukes' stages A-D or more recently according to the TNM classification. The least malignant tumors (Dukes' stages A and B) are generally associated with a relatively favorable outcome, while highly malignant tumors with metastasis (Dukes' stage C and D) have poor survival rates. Unfortunately, colorectal cancer has often grown to a considerable size before detection and thus metastases are not uncommon. The tumor typically metastasizes to regional lymph nodes, but distant metastasis to the liver and lung are also common.

Symptoms depend on where in the distal gastrointestinal tract the tumor is located, and include bowel distress, diarrhea, constipation, pain and anemia (secondary to bleeding from the tumor into the bowel). Current diagnostics are based on patient history, clinical and endoscopic examination (rectoscopy and colonoscopy), optionally followed by radiological mapping to determine extensiveness of tumor growth. In conjunction with endoscopic examination, tissue biopsies are performed from dubious lesions.

In differential diagnostics, cytokeratin 20 (CK20), an intermediate filament marker abundant in the glandular cells of the GI-tract, is commonly used to diagnose primary tumors in the GI-tract including colorectal cancer. The CK20 marker is not ideal as several other adenocarcinomas also can be positive for CK20 antibodies, whereas not all colorectal cancers are positive. Prognostic information is mainly obtained from tumor staging classification as there are no accepted grading systems or protein markers that provide additional prognostic data. Today there are no available markers that can distinguish tumors of low malignancy grade and low risk for developing into a metastasizing disease from highly malignant tumors with a reduced chance of survival. There is thus a great need for molecular markers that can be used to predict patient outcome and to guide for patient management including therapeutic intervention.

BRIEF DESCRIPTION

It is an object of some aspects of the present disclosure to provide new epitopes and affinity ligands binding thereto.

Further, an object of some aspects is to provide means and methods useful in the establishment of a prognosis for a mammalian subject having a colorectal cancer.

The present invention is defined by the appending claims.

BRIEF DESCRIPTION OF THE FIGURES

FIG. 1 shows the results of an overall survival analysis (OS) based on immunohistochemical staining of 305 subjects diagnosed with colorectal sigmoid colon carcinomas using monoclonal antibody 5E2. The solid line represents nuclear fraction 2% (NF>0), and the dotted line represents a nuclear fraction ≦2% (NF>0).

FIG. 2 shows the results of an overall survival analysis (OS) based on immunohistochemical staining of 305 subjects diagnosed with colorectal sigmoid colon carcinomas using monoclonal antibody 5E2. The solid line represents a weak, moderate or strong nuclear intensity (NI>0) and the dotted line represents an absent nuclear intensity (NI=0).

FIG. 3 shows the results of an overall survival analysis (OS) based on immunohistochemical staining of 305 subjects diagnosed with colorectal sigmoid colon carcinomas using monoclonal antibody 8F11. The solid line represents a nuclear fraction ≧75% (NF=1), and the dotted line represents nuclear fraction <75% (NF<1).

FIG. 4 shows the results of an overall survival analysis (OS) based on immunohistochemical staining of 305 subjects diagnosed with colorectal sigmoid colon carcinomas using monoclonal antibody 8F11. The solid line represents a strong nuclear intensity (NI=1), and the dotted line represents an absent, weak and moderate nuclear intensity (NI<1).

FIG. 5 shows a crosstabulation between the monoclonal antibodies 5E2 and 8F11.

FIG. 6 shows the immunohistochemical staining of two samples of colorectal carcinoma. The lower images are shown at a higher magnification.

FIG. 7 shows the immunohistochemical staining of two samples of colorectal carcinoma. The lower images are shown at a higher magnification.

DETAILED DESCRIPTION

Figure 1B:
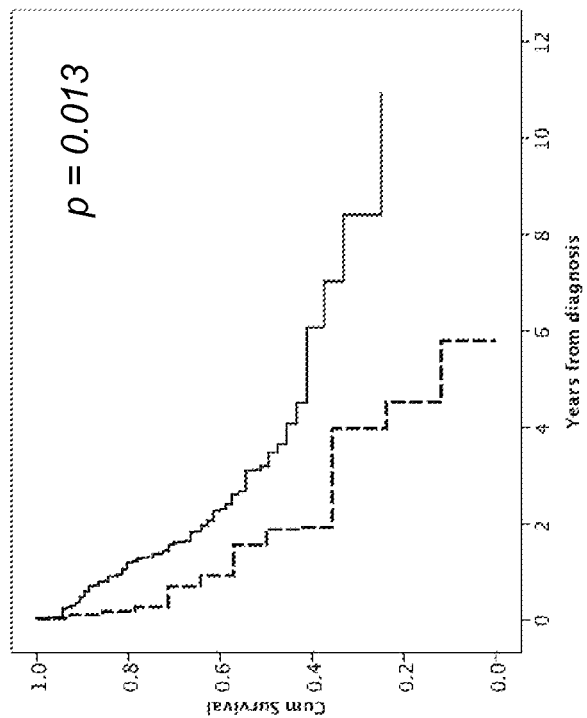
In FIG. 1B, only subjects with colorectal cancer in Duke's stage C or D were analyzed.

As a first aspect of the present disclosure, there is provided an affinity ligand capable of selective interaction with an epitope sequence consisting of 47 amino acids or less and comprising the amino acid sequence of SEQ ID NO:1 and/or SEQ ID NO:2.

In the context of the present disclosure, "selective interaction with an epitope sequence" refers to selective interaction with the amino acid residues contained in the epitope sequence. For example, an affinity ligand capable of selective interaction with an epitope sequence may be capable of selective interaction with a fragment consisting of the amino acid residues of the epitope sequence, which fragment may be present free in solution or immobilized, e.g. bound to a bead. Also, such fragment may be bound to reporter moieties for detection of interaction. As another example, "affinity ligand capable of selective interaction with an epitope sequence" may refer to the case wherein the epitope sequence is comprised in a longer polypeptide, provided that it is established that the affinity ligand interacts with the amino acid residues of the epitope sequence and not the surrounding, e.g., flanking, amino acid residues.

In the context of the present disclosure, "specific" or "selective" interaction of e.g., an affinity ligand with its target or antigen means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an affinity ligand, such as an antibody, and its antigen is from $10^{-7}$ to $10^{-11}$ M. However, high specificity does not necessarily require high affinity. Molecules with low affinity (in the molar range) for its counterpart have been shown to be as specific as molecules with much higher affinity. In the case of the present disclosure, a specific or selective interaction refers to the extent to which a particular method can be used to determine the presence and/or amount of a protein comprising a specific epitope sequence, under given conditions in the presence of other proteins in a tissue sample or fluid sample of a naturally occurring or processed biological fluid. In other words, specificity or selectivity is the capacity to distinguish between related polypeptide sequences. Specific and selective are sometimes used interchangeably in the present description. Specificity and selectivity determinations are also described in Nilsson P et al. (2005) Proteomics 5:4327-4337.

This first aspect of the present disclosure is based on that the inventors have identified certain epitopes (i.e., SEQ ID NO:1 and 2) and developed affinity ligands which bind to these epitopes. Also, the inventors have found that the affinity ligands binding to protein comprising the amino acid sequence of SEQ ID NO:1 and/or 2 may be useful for establishing a prognosis for a subject having a colorectal cancer. The expression of protein comprising SEQ ID NO:1 and/or 2 in colorectal cancer patients is shown herein to correlate with the survival of such patients. Thus, the affinity ligands of the first aspect may for example be used in various analyses, methods, assays or set-ups for establishing the prognosis for a subject having a colorectal cancer. In general in such applications, it is more desirable to have affinity ligands which are specific for a certain epitope than affinity ligands, such as polyclonal antibodies, that are only specific for a full-length protein or a longer fragment (such as an antigen) thereof. An example of an application of the affinity ligand according the first aspect is provided as aspect three below.

Antibodies interacting with the epitope having the sequence SEQ ID NO:1 have been found to be particularly suitable for establishing a prognosis for a subject having a colorectal cancer.

Consequently, in embodiments of the first aspect, the epitope sequence in question may comprise SEQ ID NO:1. For example, the inventors have found that a monoclonal antibody according to such embodiments present a stronger and more distinct immunoreactivity with tissue samples comprising protein comprising the amino acid sequence SEQ ID NO:1 than polyclonal antibodies which also bind to such protein but are not selective for the epitope sequence comprising SEQ ID NO:1 (see also FIGS. 6-7).

By means of epitope mapping using two different monoclonal antibodies, the inventors have identified two different amino acid sequences (SEQ ID NO:3 and SEQ ID NO:4) which both comprises SEQ ID NO:1. Consequently, in embodiments of the first aspect, the epitope sequence in question may comprise SEQ ID NO:3 and/or SEQ ID NO:4.

Figure 3B:
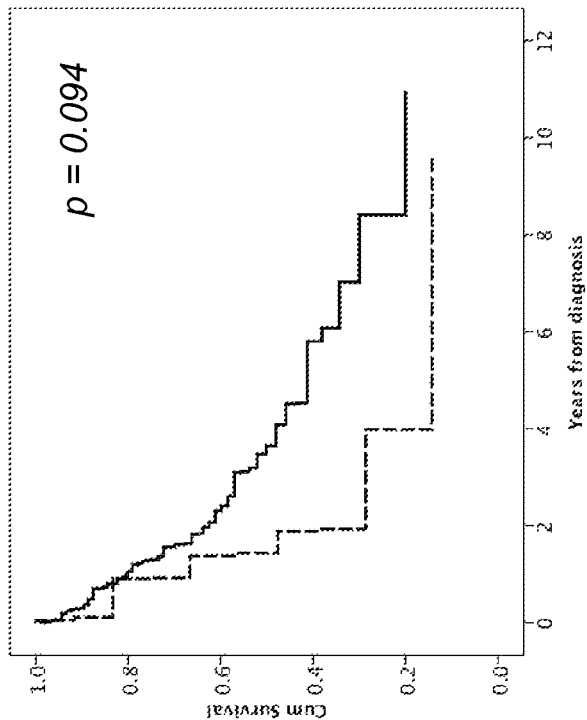
In FIG. 3B, only subjects with colorectal cancer in Duke's stage C or D were analyzed.

The monoclonal antibody used to identify SEQ ID NO:3 is shown herein to be relevant for establishing a prognosis for a subject having a colorectal cancer (see FIGS. 3 and 4). Consequently, in embodiments of the first aspect, the epitope sequence in question may comprise SEQ ID NO:3.

A number of polypeptide fragments being of the defined length, i.e., SEQ ID NO: 31-37, which all comprises SEQ ID NO:3, are shown herein to interact with that monoclonal antibody. Consequently, in embodiments of the first aspect, the epitope sequence in question may comprise or consist of an amino acid sequence selected from the group consisting of SEQ ID NO:31-37.

The monoclonal antibody used to identify SEQ ID NO:4 is shown herein to be particularly relevant for establishing a prognosis for a subject having a colorectal cancer (see FIGS. 1 and 2). Consequently, in embodiments of the first aspect, the epitope sequence in question may comprise SEQ ID NO:4.

A number of polypeptide fragments being of the defined length, i.e., SEQ ID NO: 6-14, which all comprises SEQ ID NO:4, are shown herein to interact with the particularly relevant monoclonal antibody. Consequently, in embodiments of the first aspect, the epitope sequence in question may comprise or consist of an amino acid sequence selected from the group consisting of SEQ ID NO:6-14.

By means of epitope mapping using two different monoclonal antibodies, the inventors have identified two different amino acid sequences (SEQ ID NO:2 and SEQ ID NO:5) which both comprises SEQ ID NO:2.

Consequently, in embodiments of the first aspect, the epitope sequence in question may comprise SEQ ID NO:5.

A number of polypeptide fragments being of the defined length, i.e., SEQ ID NO:52-59 and 78-82, were used in the identification of SEQ ID NO:2. Consequently, in embodiments of the first aspect, the epitope sequence in question may comprise or consist of an amino acid sequence selected from the group consisting of SEQ ID NO:52-59 and 78-82.

The above-mentioned fragments comprising SEQ ID NO:3 are 33, 38, 39, 42, 43, 45 and 47 amino acids long, respectively. Further, the above-mentioned fragments comprising SEQ ID NO:4 are 31, 34, 37, 38, 41, 42, 43, 45, and 47 amino acids long, respectively.

Consequently, in embodiments of the first aspect, the epitope sequence in question may consist of 45 amino acid residues or less, such as 43 amino acid residues or less, such as 42 amino acid residues or less, such as 41 amino acid residues or less, such as 39 amino acid residues or less, such as 38 amino acid residues or less, such as 37 amino acid residues or less, such as 34 amino acid residues or less, such as 33 amino acid residues or less, such as 31 amino acid residues or less.

However, as long as the epitope sequence comprises SEQ ID NO:1 or 2, it may not have to be that long (>30 amino acids) to enable interaction with the affinity ligand of the first aspect. Consequently, in embodiments of the first aspect, the epitope sequence may consist of 25 amino acids or less, such as 20 amino acids or less, such as 17 amino acids or less, such as 14 amino acids or less, such as 12 amino acids or less. In the epitope sequence, the amino acids flanking SEQ ID NO:1 or SEQ ID NO:2 may for example be those which are flanking them in the protein SATB2.

Once provided with the inventive epitope information disclosed herein, it is regarded as within the capabilities of those of ordinary skill in the art to select or manufacture an affinity ligand according to the first aspect. Nevertheless, examples of affinity ligands that may prove useful, as well as examples of formats and conditions for detection and/or quantification, are given below for the sake of illustration.

Thus, in some embodiments of the first aspect, the affinity ligand may be selected from the group consisting of antibodies, fragments thereof and derivatives thereof, i.e., affinity ligands based on an immunoglobulin scaffold. For example, the antibodies may be isolated and/or mono-specific. For example, antibodies comprise monoclonal and polyclonal antibodies of any origin, including murine, rabbit, human and other antibodies, as well as chimeric antibodies comprising sequences from different species, such as partly humanized antibodies, e.g., partly humanized mouse antibodies. Polyclonal antibodies are produced by immunization of animals with the antigen of choice. Monoclonal antibodies of defined specificity can be produced using the hybridoma technology developed by Köhler and Milstein (Köhler G and Milstein C (1976) Eur. J. Immunol. 6:511-519). The affinity ligand shown herein to be particularly relevant for establishing a prognosis for a subject having colorectal cancer is a monoclonal antibody. Thus, in embodiments of the first aspect, the affinity ligand may be a monoclonal antibody.

In the context of the present disclosure, a "mono-specific antibody" is one of a population of polyclonal antibodies which has been affinity purified on its own antigen, thereby separating such mono-specific antibodies from other antiserum proteins and non-specific antibodies. This affinity purification results in antibodies that bind selectively to its antigen. In the case of the present invention, the polyclonal antisera are purified by a two-step immunoaffinity based protocol to obtain mono-specific antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al. (2005) Proteomics 5:4327-4337).

Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Plückthun A (1988) Science 240:1038-1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al. (1991) Biochemistry 30:6803-6805); camelid heavy-chain dimers (Hamers-Casterman C et al. (1993) Nature 363: 446-448) and single variable domains (Cai X and Garen A (1996) Proc. Natl. Acad. Sci. U.S.A. 93:6280-6285; Masat L et al. (1994) Proc. Natl. Acad. Sci. U.S.A. 91:893-896), and single domain scaffolds like e.g., the New Antigen Receptor (NAR) from the nurse shark (Dooley H et al. (2003) Mol. Immunol. 40:25-33) and minibodies based on a variable heavy domain (Skerra A and Plückthun A (1988) Science 240:1038-1041).

Polyclonal and monoclonal antibodies, as well as their fragments and derivatives, represent the traditional choice of affinity ligands in applications requiring selective biomolecular recognition, such as in the detection and/or quantification of target protein according to the method aspects below. However, those of skill in the art know that, due to the increasing demand of high throughput generation of selective binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands according to the first aspect may be generated by combinatorial engineering of one of a plurality of possible scaffold molecules, and the affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren P A and Skerra A (2004) J. Immunol. Meths. 290:3-28), or of an oligonucleotide origin (Gold L et al. (1995) Annu. Rev. Biochem. 64:763-797).

A large number of non-immunoglobulin protein scaffolds have been used as supporting structures in development of novel binding proteins. Non-limiting examples of such structures, useful for generating affinity ligands according to the first aspect, are staphylococcal protein A and domains thereof and derivatives of these domains, such as protein Z (Nord K et al. (1997) Nat. Biotechnol. 15:772-777); lipocalins (Beste G et al. (1999) Proc. Natl. Acad. Sci. U.S.A. 96:1898-1903); ankyrin repeat domains (Binz H K et al. (2003) J. Mol. Biol. 332:489-503); cellulose binding domains (CBD) (Smith G P et al. (1998) J. Mol. Biol. 277:317-332; Lehtiö J et al. (2000) Proteins 41:316-322); γ crystallines (Fiedler U and Rudolph R, WO01/04144); green fluorescent protein (GFP) (Peelle B et al. (2001) Chem. Biol. 8:521-534); human cytotoxic T lymphocyte-associated antigen 4 (CTLA-4) (Hufton S E et al. (2000) FEBS Lett. 475:225-231; Irving R A et al. (2001) J. Immunol. Meth. 248:31-45); protease inhibitors, such as Knottin proteins (Wentzel A et al. (2001) J. Bacteriol. 183: 7273-7284; Baggio R et al. (2002) J. Mol. Recognit. 15:126-134) and Kunitz domains (Roberts B L et al. (1992) Gene 121:9-15; Dennis M S and Lazarus R A (1994) J. Biol. Chem. 269:22137-22144); PDZ domains (Schneider S et al. (1999) Nat. Biotechnol. 17:170-175); peptide aptamers, such as thioredoxin (Lu Z et al. (1995) Biotechnology 13:366-372; Klevenz B et al. (2002) Cell. Mol. Life. Sci. 59:1993-1998); staphylococcal nuclease (Norman T C et al. (1999) Science 285:591-595); tendamistats (McConell S J and Hoess R H (1995) J. Mol. Biol. 250:460-479; Li R et al. (2003) Protein Eng. 16:65-72); trinectins based on the fibronectin type III domain (Koide A et al. (1998) J. Mol. Biol. 284:1141-1151; Xu L et al. (2002) Chem. Biol. 9:933-942); and zinc fingers (Bianchi E et al. (1995) J. Mol. Biol. 247:154-160; Klug A (1999) J. Mol. Biol. 293:215-218; Segal D J et al. (2003) Biochemistry 42:2137-2148).

The above-mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as the affinity ligand according to the first aspect. Single stranded nucleic acids, called aptamers or decoys, fold into well-defined three-dimensional structures and bind to their target with high affinity and specificity. (Ellington A D and Szostak J W (1990) Nature 346:818-822; Brody EN and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of an affinity ligand according to the first aspect from a pool of variants of any of the scaffold structures mentioned above, a number of selection platforms are available for the isolation of a specific novel ligand against a target protein of choice. Selection platforms include, but are not limited to, phage display (Smith G P (1985) Science 228: 1315-1317), ribosome display (Hanes J and Plückthun A (1997) Proc. Natl. Acad. Sci. U.S.A. 94:4937-4942), yeast two-hybrid system (Fields S and Song O (1989) Nature 340: 245-246), yeast display (Gai S A and Wittrup K D (2007) Curr Opin Struct Biol 17:467-473), mRNA display (Roberts R W and Szostak J W (1997) Proc. Natl. Acad. Sci. U.S.A. 94:12297-12302), bacterial display (Daugherty PS (2007) Curr Opin Struct Biol 17:474-480, Kronqvist N et al. (2008) Protein Eng Des Sel 1-9, Harvey B R et al. (2004) PNAS101 (25):913-9198), microbead display (Nord O et al. (2003) J Biotechnol 106:1-13, WO01/05808), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments first aspect, the affinity ligand may be a non-immunoglobulin affinity ligand derived from any of the protein scaffolds listed above, or an oligonucleotide molecule.

The affinity ligand may be labeled for use in various analyses, assays, methods and set-ups. Embodiments of a labeled affinity ligand according to the first aspect are discussed below in connection with the third and fourth aspects.

The ligand according to the first aspect may be used for in vivo diagnosis, such as in vivo imaging.

The inventors have realized that target protein expression in sigmoid colon is particularly relevant for the establishment of a prognosis for a colorectal cancer. Thus, the affinity ligand may be for use in vivo for detecting expression of target protein (see definition below).

Thus, in an embodiment of the first aspect, the affinity ligand may be for use in an in vivo method for detecting expression of target protein (see definition below), e.g. for establishing a prognosis for a mammalian subject having a colorectal cancer.

In the in vivo embodiments, the affinity ligand may for example be labeled for enabling imaging, i.e. labeled with a detectable label such as a radioactive isotope. Appropriate labels for labeling affinity ligands, such as antibodies, are well known to the skilled person. Consequently, the in vivo method for establishing a prognosis for a mammalian subject having a colorectal cancer may for example reveal expression of target protein in a tumor in vivo, which in turn may form the basis of a treatment decision.

As shown herein, the affinity ligand according to the first aspect may have various applications related to the establishment of a prognosis for a subject having a colorectal cancer. Consequently, as a second aspect of the present disclosure, there is provided a use of an affinity ligand according to the first aspect as a prognostic agent.

In the context of the present disclosure, a "prognostic agent" refers to an agent having at least one property being valuable in an establishment of a prognosis. For example the "prognostic agent" may be capable of selective interaction with a prognostic marker, such as a marker protein.

Further, in the context of the present disclosure, a "prognostic marker" refers to a something material which presence is of value in an establishment of a prognosis. For example, the prognostic marker may be a target protein as defined below.

In embodiments of the second aspect, the use may be for establishing a prognosis for a mammalian subject having a cancer, such as a colorectal cancer.

As a third aspect of the present disclosure, there is provided a method for determining whether a prognosis for a mammalian subject having a colorectal cancer is worse than or equal to a reference prognosis, comprising the steps of:
a) providing a sample earlier obtained from said subject;
b) evaluating the amount of target protein present in at least part of said sample using an affinity ligand according to the first aspect, and determining a sample value corresponding to said evaluated amount;
c) comparing said sample value obtained in step d) with a reference value associated with said reference prognosis; and, if said sample value is lower than or equal to said reference value,
d) concluding that said prognosis for said subject is worse than or equal to said reference prognosis.

In the context of the aspects one to seven of the present disclosure, "target protein" refers to protein comprising the amino acid sequence of SEQ ID NO:1 and/or SEQ ID NO:2. SATB1 protein and SATB2 protein are examples of proteins comprising the amino acid sequence of SEQ ID NO:1 and/or SEQ ID NO:2. In an embodiment, the target protein may be SATB2, which comprises SEQ ID NO:1.

According to a first configuration of the third aspect, there is provided a method for determining a prognosis for a mammalian subject having a colorectal cancer, comprising the steps of:
a) providing a sample earlier obtained from said subject;
b) evaluating the amount of target protein present in at least part of said sample using an affinity ligand according to the first aspect, and determining a sample value corresponding to said evaluated amount;
c) comparing said sample value obtained in step d) with a reference value associated with a reference prognosis; and, if said sample value is lower than or equal to said reference value,
d) concluding that said prognosis for said subject is worse than or equal to said reference prognosis.

In embodiments, any one of the above methods may comprise the additional step:
if the sample value is higher than the reference value,
e) concluding that the prognosis for the subject is better than the reference prognosis.

According to a second configuration of the third aspect, there is provided a method for determining whether a prognosis for a mammalian subject having a colorectal cancer is worse than or equal to a reference prognosis or whether it is better than said reference prognosis, said method comprising the steps of:
a) providing a sample earlier obtained from said subject;
b) evaluating the amount of target protein present in at least part of said sample using an affinity ligand according to the first aspect, and determining a sample value corresponding to said evaluated amount;
c) comparing said sample value obtained in step d) with a reference value associated with a reference prognosis; and, if said sample value is equal to or lower than said reference value, d1) concluding that the prognosis for said subject is equal to or worse than said reference prognosis, or if said sample value is higher than said reference value, d2) concluding that the prognosis for said subject is better than said reference prognosis.

However closely related and covered by the same concept, d1) and d2) of the second configuration of the third aspect provide two alternative conclusion options. Accordingly, the method of the second configuration of the third aspect may answer the question whether the prognosis for said subject is equal to or worse than said reference prognosis or the question whether the prognosis for said subject is better than said reference prognosis. However, the method of the second configuration of the third aspect may also, but does not have to, comprise both step d1), together with it's adherent qualification ("if phrase"), and step d2), together with it's adherent qualification ("if phrase").

Consequently, the third aspect is limited to the use of an affinity ligand according to the first aspect, i.e. to the recognition of the epitopes of the present disclosure. For example, the third aspect may provide a tool for the identification of aggressive forms of colorectal cancer, and in turn, early identification of aggressive forms of colorectal cancer is of vital importance as it helps a physician selecting an appropriate treatment strategy. Also, by identifying less aggressive forms at an early stage, over-treatment may be avoided.

In the present disclosure, different protein expression values (sample values) corresponding to various prognoses are presented. Typically, a low sample value is associated with a poorer prognosis than a high sample value. In the above methods, the sample value is compared to a reference value, and if the sample value is equal to or lower than the reference value, it is concluded that the prognosis for the subject is equal to or worse than a reference prognosis associated with the reference value.

Consequently, the above methods may be adapted to a reference value. In such case, starting from a given sample value which under certain circumstances is considered to be relevant, a reference value which is equal to, or higher than, the given sample value, may be selected. Subsequently, a reference prognosis being associated with that reference value may be established. Guided by the present disclosure, the person skilled in the art understands how to establish a reference prognosis which corresponds to a given reference value. For example, the relation between protein expression values and survival data in a group of cancer patients may be examined as in Examples, Section 4, below, and the procedure described therein may be adapted to a given reference value. Then, a prognosis corresponding to the given reference value may be selected as the reference prognosis.

Also, the above method may be adapted to a given reference prognosis. In such case, starting from a given reference prognosis which under certain circumstances is considered to be relevant, for example for selecting an appropriate therapy, a corresponding reference value may be established. Guided by the present disclosure, the person skilled in the art understands how to establish a reference value which corresponds to a given reference prognosis. For example, the relation between sample values and survival data in a group of cancer patients may be examined as in Examples, Section 4, below, but the procedure described therein is adapted to establish reference values corresponding to a given reference prognosis. For example, different reference values may be tested until one which correlates with the given reference prognosis is found. A skilled person may do such testing without undue burden, e.g., because the present disclosure presents suitable starting values which may reduce the required amount of testing.

Accordingly, in embodiments of the methods of the above aspect, the reference prognosis may be based on a previously established prognosis, e.g. obtained by an examination of the same subject or population of subjects. Also, the reference prognosis may be adapted to a background risk in the general population, a statistical prognosis/risk or an assumption based on an examination of the subject. Such examination may take into account the subject's age, general condition, sex, race and/or medical status and history, such as cancer history or colorectal cancer status. For example, a physician may adapt the reference prognosis to the subject's cancer history, the stage of the tumor, the morphology of the tumor, the location of the tumor, the presence and spread of metastases and/or further cancer characteristics.

According to a third configuration of the third aspect, there is provided a method for establishing a prognosis for a mammalian subject having a colorectal cancer:

a) providing a sample from the subject;

b) evaluating the amount of target protein present in at least part of said sample using an affinity ligand according to the first aspect, and determining a sample value corresponding to said evaluated amount;

c) correlating the sample value of step b) to the prognosis for the subject.

In the context of the present disclosure, "establishing a prognosis" refers to establishing a specific prognosis or a prognosis interval.

In an embodiment of the above method, the sample may be an earlier obtained sample.

The correlating of step c) refers to any way of associating survival data to the obtained sample value so as to establish a prognosis for the subject.

The identified correlation between the binding activity of the affinity ligand according to the first aspect and colorectal cancer prognoses may also form the basis for a treatment decision. For example, a method based on such a correlation may suggest a treatment regime that otherwise would not have been considered. Thus, according to a fourth aspect of the present disclosure, there is provided a method of treatment of a subject being in need thereof, wherein the subject is having a colorectal cancer, comprising the steps of:

a) providing a sample from said subject;

b) evaluating the amount of target protein present in at least part of said sample using an affinity ligand according to the first aspect, and determining a sample value corresponding to said evaluated amount;

c) comparing said sample value obtained in step b) with a reference value; and, if said sample value is lower than or equal to said reference value, d) treating said subject with an adjuvant colorectal cancer treatment regimen.

In an embodiment of the second aspect, the method may comprise the additional step:

and if said sample value is higher than said reference value, e) refraining from treating said subject with the adjuvant colorectal cancer treatment regimen.

In one embodiment of the fourth aspect, the reference value of step c) may be associated with a reference prognosis and said colorectal cancer treatment regimen of step d) may be adapted to a prognosis which is worse than or equal to the reference prognosis. In such an embodiment, the method may comprise the additional step: e) and if said sample value is higher than said reference value, treating said subject with a treatment regimen adapted to a prognosis which is better than the reference prognosis.

For example, the treatment regimen of the second aspect may be selected from chemotherapy, neo-adjuvant therapy and combinations thereof.

Thus, the treatment regimen may be neo-adjuvant therapy. Such neo-adjuvant therapy may consist of radiation therapy only or radiation therapy in combination with chemotherapy.

In general, when deciding on a suitable treatment strategy for a patient having colorectal cancer, the physician responsible for the treatment may take several parameters into account, such as the result of an immunohistochemical evaluation, the patient's age, general condition, tumor stage, vascular invasion and differentiation grade. To be guided in such decision, the physician may perform a test, or order a test performed, according to an embodiment of any of the method aspects presented above.

In the context of the present disclosure, "prognosis" refers to the prediction of the course or outcome of a disease and its treatment or to the survival of the subject suffering from the disease. For example, prognosis may refer to a determination of chance of survival or recovery from a disease, as well as to a prediction of the expected survival time of a subject. It may also be the likelihood of disease recurrence, e.g., local, regional or distant events. Further, a prognosis may involve establishing the likelihood for survival of a subject during a period of time into the future, such as three years, five years, ten years, fifteen years or any other period of time. Consequently, the prognosis for a subject may for example be a probability of survival, such as "overall survival", which is a recognized survival measure.

In the methods above involving a prognosis and a reference prognosis, these two prognoses are the same type of prognosis. As an example, if the reference prognosis is a reference probability of over-all survival, it follows that the conclusion will be a probability of over-all survival for the subject, which will be in relation to the reference probability over-all survival.

Thus, in embodiments of the methods of the third and, if applicable, fourth aspect, the prognosis may be a probability of survival, which entails that the prognosis for the subject is a probability of survival and the reference prognosis is a probability of survival. For example, the probability of survival may be a probability of five-year survival, ten-year survival or 15-year survival.

Further, in the context of the present disclosure, "a mammalian subject having a colorectal cancer" refers to a mammalian subject having a primary or secondary colorectal tumor or a mammalian subject which has had a tumor removed from the colon and/or rectum, wherein the removal of the tumor refers to killing or removing the tumor by any appropriate type of surgery or therapy. For example, in the case in which the subject has had the tumor removed, the tumor may have been removed less than five years ago, such as less than one year or six months ago. In the method and use aspects of the present disclosure, "a mammalian subject having a colorectal cancer" also includes the cases wherein the mammalian subject is suspected of having a colorectal cancer at the time of the performance of the use or method and the colorectal cancer diagnosis is established later.

In the context of the method aspects of the present disclosure, "earlier obtained" refers to obtained before the method is performed. Consequently, if a sample earlier obtained from a subject is provided in a method, the method does not involve obtaining the sample from the subject, i.e., the sample was previously obtained from the subject in a step separate from the method.

Accordingly, all methods and uses of the present disclosure, may be performed entirely in vitro.

Step b) of the above method aspects of the present disclosure involve evaluating the amount of a protein present in at least part of the sample, and determining a sample value corresponding to the amount. The "at least part of the sample" refers to a relevant part, or relevant parts, of the sample for establishing the prognosis or drawing conclusions regarding suitable treatments. The person skilled in the art understands which part or parts that are relevant under the circumstances present when performing the method. For example, if the sample comprises tumor and non-tumor cells, the skilled person may only consider the tumor cells, and only the nuclei of the tumor cells, of the sample.

Further, in step b) an amount is evaluated and a sample value corresponding to the amount is determined. Consequently, an exact measurement of the amount of the protein is not required for obtaining the sample value. For example, the amount of the protein may be evaluated by visual inspection of a stained tissue sample and the sample value may then be categorized, e.g., as high or low, based on the evaluated amount. The person skilled in the art understands how to perform such evaluation and determination.

Also regarding step b) of the methods according to the above aspects, an increase in the amount of the protein typically results in an increase in the sample value. However, in some embodiments, the evaluated amount may correspond to any of a predetermined number of discrete sample values. In such embodiments, an first amount and a second, increased, amount, may correspond to the same sample value. In any case, an increase in the amount of the protein will not result in a decrease in the sample value in the context of the methods according to the above aspects.

However inconvenient, but in an equivalent fashion, the evaluated amounts may be inversely related to sample values if the qualification between step c) and d) is "if the sample value is higher than or equal to the reference value".

Still further, in the context of the present disclosure, the "reference value" refers to a predetermined value which is relevant for making decisions, or drawing conclusions, regarding the prognosis for or treatment of the subject.

Also, in the context of the present disclosure, a reference prognosis being "associated" with a reference value refers to the reference value being assigned to the reference prognosis, based on empirical data and/or clinically relevant assumptions. See e.g., step c) of the methods of the third, and certain embodiments of the fourth, aspect. The reference value does not have to be assigned to a reference prognosis directly derived from prognosis data of a group of subjects exhibiting the reference value. The reference prognosis may for example correspond to the prognosis for subjects exhibiting the reference value or lower. That is, if the reference value is 1 on a scale from 0 to 3, the reference prognosis may be the prognosis of the subjects exhibiting the values 0 or 1. Consequently, the reference prognosis may also be adapted to the nature of the available data. As further discussed above, the reference prognosis may be adapted to other parameters as well.

Various conditions may be used for the evaluation in step b) to obtain said sample value. In embodiments of the methods of aspects three and four, step b) may comprises applying said affinity ligand to said sample under conditions that enable binding of said affinity ligand to protein in said sample, and said evaluated amount is obtained by evaluating an amount of said affinity ligand that is in association with said at least part of said sample. Here, the "association" refers to specific and/or selective interaction between the affinity ligand and components, e.g., proteins, in the sample.

In embodiments of the methods of aspects three and four, step b) may comprise the steps of:

b1) applying said affinity ligand to said sample during said conditions that enable binding of said affinity ligand to protein in said sample;

b2) removing non-bound affinity ligand from said sample; and b3) evaluating the amount of affinity ligand remaining in association with said at least part of said sample to obtain said evaluated amount.

Here, "affinity ligand remaining in association with the sample" refers to affinity ligand which was not removed in step b2), e.g., the affinity ligand bound to the sample. The binding may for example be specific and/or selective interaction between antibody and antigen present in the sample. Further, in such embodiments, step b2) may for example be washing with washing buffers. Examples of washings buffers are well known to the skilled person. Also, the sample in such embodiments may be a tissue sample, and in such case, steps b1)-b3) reflects a staining procedure. For example, washings is such a procedure is a standard operation within the art.

In some embodiments of the methods of aspects three and four, the affinity ligand may be detectable and/or quantifiable. The detection and/or quantification of such an affinity ligand may be accomplished in any way known to the skilled person for detection and/or quantification of binding reagents in assays based on biological interactions. Thus, any affinity ligand, as described above, may be used quantitatively or qualitatively to detect the presence of target protein. These "primary" affinity ligands may be labeled themselves with various markers or may in turn be detected by secondary, labeled affinity ligands to allow detection, visualization and/or quantification. This can be accomplished using any one or more of a multitude of labels, which can be conjugated to the affinity ligand capable of interaction with target protein or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g., fluorescein, rhodamine, phycoerythrin, fluorescamine), chromophoric dyes (e.g., rhodopsin), chemiluminescent compounds (e.g., luminal, imidazole) and bioluminescent proteins (e.g., luciferin, luciferase), haptens (e.g., biotin). A variety of other useful fluorescers and chromophores are described in Stryer L (1968) Science 162:526-533 and Brand L and Gohlke J R (1972) Annu. Rev. Biochem. 41:843-868. Affinity ligands can also be labeled with enzymes (e.g., horseradish peroxidase, alkaline phosphatase, beta-lactamase), radioisotopes (e.g., $^{3}H$, $^{14}C$, $^{32}P$, $^{35}S$ or $^{125}I$ and particles (e.g., gold). In the context of the present disclosure, "particles" refer to particles, such as metal particles, suitable for labeling of molecules. Further, the affinity ligands may also be labeled with fluorescent semiconductor nanocrystals (quantum dots). Quantum dots have superior quantum yield and are more photostable compared to organic fluorophores and are therefore more easily detected (Chan et al. (2002) Curr Opi Biotech. 13: 40-46). The different types of labels can be conjugated to an affinity ligand using various chemistries, e.g., the amine reaction or the thiol reaction. However, other reactive groups than amines and thiols can be used, e.g., aldehydes, carboxylic acids and glutamine.

The method aspects of the present disclosure may be put to use in any of several known formats and set-ups, of which a non-limiting selection is discussed below.

In a set-up based on histology, the detection, localization and/or quantification of a labeled affinity ligand bound to target protein may involve visualizing techniques, such as light microscopy or immunofluoresence microscopy. Other methods may involve the detection via flow cytometry or luminometry.

A biological sample, such as a tumor tissue sample (biopsy), for example from colorectal tissue, which has been removed from the subject may be used for detection and/or quantification of target protein. The biological sample, such as the biopsy, may be an earlier obtained sample. If using an earlier obtained sample in a method, no steps of the method are practiced on the human or animal body. The affinity ligand may be applied to the biological sample for detection and/or quantification of target protein. This procedure enables not only detection of target protein, but may in addition show the distribution and relative level of expression thereof.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light in a specific wavelength region. The presence of a luminescently tagged affinity ligand may be detected and/or quantified by luminescence developed during a chemical reaction. Detection of an enzymatic reaction is due to a color shift in the sample arising from chemical reaction. Those of skill in the art are aware that a variety of different protocols can be modified in order for proper detection and/or quantification.

In embodiments of the methods of aspects three and four, a biological sample may be immobilized onto a solid phase support or carrier, such as nitrocellulose or any other solid support matrix capable of immobilizing target protein present in the biological sample applied to it. Some well-known solid state support materials useful in the present invention include glass, carbohydrate (e.g., Sepharose), nylon, plastic, wool, polystyrene, polyethene, polypropylene, dextran, amylase, films, resins, cellulose, polyacrylamide, agarose, alumina, gabbros and magnetite. After immobilization of the biological sample, primary affinity ligand according to the first aspect may be applied, e.g., as described in Examples, Sections 4 or 5, of the present disclosure. If the primary affinity ligand is not labeled in itself, the supporting matrix may be washed with one or more appropriate buffers known in the art, followed by exposure to a secondary labeled affinity ligand and washed once again with buffers to remove unbound affinity ligands. Thereafter, selective affinity ligands may be detected and/or quantified with conventional methods. The binding properties for an affinity ligand may vary from one solid state support to the other, but those skilled in the art should be able to determine operative and optimal assay conditions for each determination by routine experimentation.

Consequently, in embodiments of the methods aspects three and four, the affinity ligand applied in b1) (primary affinity ligand) may be detected using a secondary affinity ligand capable of recognizing the quantifiable affinity ligand. The quantification of b3) may thus be carried out by means of a secondary affinity ligand with affinity for the primary affinity ligand. As an example, the secondary affinity ligand may be an antibody or a fragment or a derivative thereof.

As an example, one available method for detection and/or quantification of target protein is by linking the affinity ligand according to the first aspect to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to the affinity ligand, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the present disclosure are $^{3}H$, $^{14}C$, $^{32}P$, $^{35}S$ or $^{125}I$. The specific activity of the labeled affinity ligand is dependent upon the half-life of the radiolabel, isotopic purity, and how the label has been incorporated into the affinity ligand. Affinity ligands are preferably labeled using well-known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize target protein by detection of radioactivity in vivo or in vitro. Radionuclear scanning with e.g., gamma camera, magnetic resonance spectroscopy or emission tomography function for detection in vivo and in vitro, while gamma/beta counters, scintillation counters and radiographies are also used in vitro.

In embodiments of the methods of aspects three and four, the subject may have colorectal cancer in different forms and/or stages.

In some embodiments of these aspects, the colorectal cancer in question is a node-negative colorectal cancer, i.e. colorectal cancer that has not progressed to the lymph node metastazing stage. In other similar embodiments, the colorectal cancer in question is characterized as being in either Dukes' stage A or B. In yet other embodiments, the colorectal cancer in question is colorectal adenoma or colorectal carcinoma. In these embodiments, determining that the subject exhibits low target protein expression may be of great value for the prognosis of future progression of the disease and thus form the basis for an informed decision with regard to future disease management. Within a group of subjects afflicted with such a comparatively early stage of disease, subjects with low target protein expression probably are at a comparatively high risk of developing a more aggressive disease. Low target protein expression among subjects having node-negative colorectal cancer or Dukes' stage A or B colorectal cancer may therefore indicate that these subjects should be monitored more closely and/or treated differently than subjects that do not exhibit low target protein expression. The methods according to the invention therefore offers the possibility of a greater chance for survival over a certain period of time and/or longer survival time for such subjects, owing to the additional prognostic information given by the method using the affinity ligand according to the first aspect. Subjects having a Dukes' stage A colorectal cancer are traditionally not treated with adjuvant chemotherapy. However, guided by the teachings of the present disclosure, a physician may decide to give such a subject having low, or absent, target protein expression such an adjuvant chemotherapy.

Consequently, in embodiments of the methods of aspects three and four, the colorectal cancer is in Dukes' stage A. In an alternative or complementary embodiment, said colorectal cancer is in T1-2, N0 and M0 according to the TNM staging system described above.

Further, as shown herein, the target protein expression analysis is relevant for establishing a prognosis for a subject having a colorectal cancer in Dukes' stage C or D (see FIGS. 1B, 2B, 3B and 4B). Subjects having a colorectal cancer in such an advanced stage have frequently been treated with regimens having severe side-effects. As an example, if such subjects are diagnosed with a relatively high expression of target protein, they may be given a less extensive treatment having fewer or less severe side-effects.

In embodiments of the methods of aspects three and four, the sample may be a body fluid sample. For example, the body fluid sample may be selected from the group consisting of blood, plasma, serum, cerebral fluid, urine, semen and exudate. Alternatively, the sample may be a cytology sample or a stool sample.

In further embodiments of the methods of aspects three and four, the sample may be a tissue sample, such as a colorectal tissue sample, e.g. a sample derived from the colon or rectum. For example, the tissue sample may be derived from the sigmoid colon. The inventors have realized that target protein expression in this part of colon/rectum is particularly relevant for the establishment of a prognosis for a colorectal cancer. In the art, the sigmoid colon is sometimes also referred to as the pelvic colon or sigmoid flexture.

In complementing embodiments of the methods of aspects three and four, the sample may be a tumor tissue sample.

In embodiments of the methods of aspects three and four, the sample may comprise glandular cells from said subject. Consequently, in addition to tissue samples, e.g. a stool sample or blood sample may also comprise such cells, which expression of target protein may be evaluated using the affinity ligand according to the first aspect.

The inventors have found that target protein is expressed in the nucleus of relevant cells. Consequently, the evaluation of target protein expression in a sample may be limited to an analysis of nuclear expression in tumor cells present in the sample, e.g. an earlier obtained tumor tissue biopsy material or specimen from a surgical removal of a colorectal cancer. As an example, the evaluation of step b) of the above methods may be limited to evaluating the amount of target protein in the nuclei of tumor cells, such as tumor cells originating from epithelial cells, e.g. glandular cells, of said sample. When the evaluation is limited to the nucleus, only the characteristics, such as the interaction of the affinity ligand with the nuclei is considered in the evaluation. Such evaluation may for example be an immunohistochemical staining. Further, the inventors have found that the nuclear expression of target protein may be relevant for prognostics.

A sample value of target protein being higher than the reference value, or a subject from which such sample value is obtained, is sometimes referred to herein as "target protein high". Further, a sample value of target protein being lower than or equal to the reference value, or a subject from which such sample value is obtained, is sometimes referred to herein as "target protein low".

In the context of the present disclosure, the terms "sample value" and "reference value" are to be interpreted broadly. The quantification of target protein to obtain these values may be done via automatic means, via a scoring system based on visual or microscopic inspection of samples, or via combinations thereof as long as an antibody according to the first aspect is employed. However, it is also possible for a skilled person, such as a person skilled in the art of histopathology, to determine the sample and reference values merely by inspection, e.g., of tissue slides that have been stained for target protein expression using the affinity ligand in question. The determination of the sample value being higher than the reference value may thus correspond to the determination, upon visual or microscopic inspection, that a sample tissue slide is more densely stained and/or exhibit a larger fraction of stained cells than is the case for a reference tissue slide. The sample value may also be compared to a reference value given by a literal reference, such as a reference value described in wording. Consequently, the sample and/or reference values may be thought of as mental values that the skilled person determines upon inspection and comparison.

For example, the skilled person may categorize a sample as being target protein high or low, wherein the sample is categorized as high if it contains more target protein than a previously inspected reference sample and low if it contains less or equally much. Such evaluation may be assisted by staining the sample, and, if necessary, a reference sample, with a staining solution comprising antibodies according to the first aspect.

A reference value found to be relevant for the provision of a prognosis for a subject having a colorectal cancer, or for making treatment decisions regarding such subjects, for use as comparison with the sample value from the subject, may be provided in various ways. With the knowledge of the teachings of the present disclosure, the skilled artisan can, without undue burden, provide relevant reference values for performing the methods of aspects three and four.

The person performing the methods of aspects three and four may, for example, adapt the reference value to desired prognostic information. For example, the reference value may be adapted to yield significant prognostic information, e.g., the largest separation between the high survival curve and the low survival curve (see the figures).

Alternatively, the reference value may be adapted to identify a group of subjects having a predetermined prognosis, e.g., the group of subjects having a probability of five-year overall survival of lower than a predetermined percentage.

In embodiments of the methods of aspects three and four, the reference value may correspond to the amount of target protein expression in a healthy tissue, such as healthy breast or stroma tissue, of the subject of the method. As another example, the reference value may be provided by the amount of target protein expression measured in a standard sample of normal tissue from another, comparable subject. As another example, the reference value may be provided by the amount of target protein expression measured in a reference sample comprising tumor cells, such as a reference sample of tumor tissue, e.g., colorectal cancer tissue. The amount of target protein expression of the reference sample may preferably be previously established. Consequently, the reference value may be provided by the amount of target protein measured in a reference sample comprising cells expressing a predetermined amount of target protein.

Further, the reference value may for example be provided by the amount of target protein expression measured in a reference sample comprising cell lines, such as cancer cell lines, expressing a predetermined, or controlled, amount of target protein. The person skilled in the art understands how to provide such cell lines, for example guided by the disclosure of Rhodes et al. (2006) *The biomedical scientist*, p 515-520.

Consequently, in embodiments of the methods of aspects three and four, the reference value may be a predetermined value corresponding to the amount of target protein expression in a reference sample.

However, as discussed further below, the amount of target protein in the reference sample does not have to directly correspond to the reference value. The reference sample may also provide amounts of target protein that help a person performing the method to assess various reference values. For example, the reference sample(s) may help in creating a mental image of the reference value by providing a "positive" (high) and/or a "negative" (low) value.

The inventors show herein that subjects who suffer from colorectal cancer and have essentially no target protein expression generally have a relatively poor prognosis (see e.g. FIG. 1). Thus, in embodiments of the methods of aspects three and four, the sample value of step b) may be either 1, corresponding to detectable target protein in the sample, or 0, corresponding to no detectable target protein in the sample. Consequently, in such embodiments, the evaluation of the sample is digital: target protein is considered to be either present or not. In the context of the present disclosure, "no detectable target protein" refers to an amount of target protein that is so small that it is not, during normal operational circumstances, detectable by a person or an apparatus performing the method according to any one of aspects three and four. The "normal operational circumstances" refer to the laboratory methods and techniques a person skilled in the art would find appropriate for performing the invention.

Accordingly, in embodiments of the methods of aspects three and four, the reference value of step c) may be 0. And it follows that, in further embodiments of the methods of aspects three and four, the reference value of step c) may correspond to a reference sample having no detectable target protein. This means that the reference value may be obtained by analysis of a reference sample lacking target protein.

One alternative for the quantification of target protein expression in a sample, such as the sample earlier obtained from the subject or the reference sample, is the determination of the fraction of cells in the sample that exhibit target protein expression over a certain level. The fraction may for example be: a "cellular fraction", wherein the target protein expression of the whole cells is taken into account; a "cytoplasmic fraction", wherein the target protein expression of only the cytoplasms of the cells is taken into account; or a "nuclear fraction", wherein the target protein expression of only the nuclei of the cells is taken into account. The nuclear fraction may for example be classified as <2%, 2-25%, >25-75% or >75% immunoreactive cells of the relevant cell population. Alternatively, or as a complement, the nuclear fraction may be classified as $\leq$10% or >10-100%, or as $\leq$1% or >1-100%. The "nuclear fraction" corresponds to the percentage of relevant cells in a sample that exhibits a positive staining in the nucleus, wherein a medium or distinct and strong immunoreactivity in the nucleus is considered positive and no or faint immunoreactivity in the nucleus is considered negative. The person skilled in the art of pathology understands which cells that are relevant under the conditions present when performing the method and may determine a nuclear fraction based on his general knowledge and the teachings of the present disclosure. The relevant cells may for example be tumor cells. Further, the skilled artisan understands how to perform corresponding measurements employing the "cellular fraction" or the "cytoplasmic fraction".

Another alternative for the quantification of target protein expression in a sample, such as the sample earlier obtained from the subject or the reference sample, is the determination of the overall staining intensity of the sample. The intensity may for example be: a "cellular intensity", wherein the target protein expression of the whole cells is taken into account; a "cytoplasmic intensity", wherein the target protein expression of only the cytoplasms of the cells is taken into account, or a "nuclear intensity", wherein the target protein expression of only the nuclei of the cells is taken into account. Nuclear intensity is subjectively evaluated in accordance with standards used in clinical histopathological diagnostics. Outcome of a nuclear intensity determination may be classified as: absent=no overall immunoreactivity in the nucleus of relevant cells of the sample, weak=faint overall immunoreactivity in the nucleus of relevant cells of the sample, moderate=medium overall immunoreactivity in the nucleus of relevant cells of the sample, or strong=distinct and strong overall immunoreactivity in the nucleus of relevant cells of the sample. The person skilled in the art understands which cells that are relevant under the conditions present when performing the method and may determine a nuclear intensity based on his general knowledge and the teachings of the present disclosure. The relevant cells may for example be tumor cells. Further, the skilled artisan understands how to perform corresponding measurements employing the "cellular intensity" or the "cytoplasmic intensity".

The inventors have found that the nuclear expression of target protein is particularly relevant for establishing a prognosis. Thus, in embodiments of the methods of aspects three and four, the reference value may be a nuclear fraction, a nuclear intensity or a combination thereof. Accordingly, the sample value may be a nuclear fraction, a nuclear intensity or a combination thereof.

Preferably, the sample value and the reference value are both the same type of value. Accordingly, in embodiments of the methods of aspects three and four, the sample value and the reference value may each be a nuclear fraction, a nuclear intensity or a combination thereof.

In embodiments of the methods of aspects three and four, the criterion for the conclusion in step d) may be a sample value for the nuclear fraction of target protein positive cells, i.e., a "nuclear fraction", which is lower than or equal to a reference value which is 90%, such as lower than or equal to 80%, such as lower than or equal to 70%, such as lower than or equal to 60%, such as lower than or equal to 50%, such as lower than or equal to 40%, such as lower than or equal to 35%, such as lower than or equal to 30%, such as lower than or equal to 25%, such as lower than or equal to 20%, such as lower than or equal to 15%, such as lower than or equal to 10%, such as lower than or equal to 5%, such as lower than or equal to 2%, such as lower than or equal to 1%, such as equal to 0%.

In alternative or complementing embodiments of the methods of the above aspects, the reference value of step c) is a nuclear fraction of 90% or lower, such as 80% or lower, such as 70% or lower, such as 60% or lower, such as 50% or lower, such as 40% or lower, such as 35% or lower, such as 30% or lower, such as 25% or lower, such as 20% or lower, such as 15% or lower, such as 10% or lower, such as 5% or lower, such as 2% or lower, such as 1% or lower, such as 0%.

Further, in embodiments of the methods of aspects three and four, the criterion for the conclusion in step d) may be a sample value for staining intensity of a sample, i.e., a nuclear intensity, which is lower than or equal to a moderate nuclear intensity, such as lower than or equal to a weak nuclear intensity, such as an absent nuclear intensity. In alternative or complementing embodiments of the methods of aspects three and four, the reference value of step c) may be an moderate nuclear intensity of target protein expression or lower, such as a weak nuclear intensity of target protein expression or lower, such as an absent nuclear intensity of target protein expression.

Further, in embodiments of the methods of aspects three and four, the reference value may be constituted of two values, wherein the criterion for the conclusion in step d) is a sample value being higher than any one of these two values.

Alternatively, in embodiments of the methods of aspects three and four, the reference value may be a combination of a fraction value and an intensity value, such as a nuclear fraction value and a nuclear intensity value.

Also, in embodiments of the methods of aspects three and four, the reference value may be a function of a nuclear fraction value and a nuclear intensity value. For example, such a function may be a staining score. The "staining score" is calculated as described in Examples, Section 3 and Table 1 below. For example, the reference value may be a staining score of 0, 1 or 2.

The person skilled in the art realizes that other reference values being an intensity value or a fraction value also fall within the scope of the present invention. Likewise, the person skilled in the art realizes that other combinations of fractions and intensities also fall within the scope of the present invention. Consequently, the reference value may involve two, and possibly even more, criteria.

In general, the selection of a nuclear intensity value and/or a nuclear fraction value as the reference value may depend on the staining procedure, e.g., on the nature of the applied antibody according to the first invention and on the staining reagents.

Guided by the present disclosure, a person skilled in the art, e.g., a pathologist, understands how to perform the evaluation yielding a fraction, such as a cellular, cytoplasmic or nuclear fraction, or an intensity, such as a cellular, cytoplasmic or nuclear intensity. For example, the skilled artisan may use a reference sample comprising a predetermined amount of target protein for establishing the appearance of a certain fraction or intensity.

However, a reference sample may not only be used for the provision of the actual reference value, but also for the provision of an example of a sample with an amount of target protein that is higher than the amount corresponding to the reference value. As an example, in histochemical staining, such as in immunohistochemical staining, the skilled artisan may use a reference sample for establishing the appearance of a stained sample having a high amount of target protein, e.g., a positive reference. Subsequently, the skilled artisan may assess the appearances of samples having lower amounts of target protein, such as the appearance of a sample with an amount of target protein corresponding to the reference value. In other words, the skilled artisan may use a reference sample to create a mental image of a reference value corresponding to an amount of target protein which is lower than that of the reference sample. Alternatively, or as a complement, in such assessments, the skilled artisan may use another reference sample having a low amount of target protein, or essentially lacking target protein, for establishing the appearance of such sample, e.g., as a "negative reference".

For example, if a reference value of 10% nuclear fraction is used, a first reference sample having no detectable target protein, and thus corresponding to a nuclear fraction of 0, which is lower than the reference value, may be used together with a second reference sample having an amount of target protein corresponding to a nuclear fraction of 75% or higher, which is higher than the reference value.

Consequently, in the evaluation, the skilled artisan may use a reference sample for establishing the appearance of a sample with a high amount of target protein. Such reference sample may be a sample comprising tissue expressing a high amount of target protein, such as a sample comprising colorectal tumor tissue having a pre-established high expression of target protein.

Accordingly, the reference sample may provide an example of a strong nuclear intensity (NI). With the knowledge of the appearance of a sample with strong NI, the skilled artisan may then divide samples into other NI categories, such as the above-mentioned absent, weak, moderate and strong. This division may be further assisted by a reference sample lacking detectable target protein (negative reference), i.e., a reference sample providing an absent nuclear intensity. Also, the reference sample may provide an example of a sample with a nuclear fraction (NF) of 75% or higher. With the knowledge of the appearance of a sample with more than 75% positive cells, the skilled artisan may then evaluate the nuclear fraction of other samples having e.g., a lower percentage of positive cells. This division may be further assisted by a reference sample essentially lacking target protein (negative reference), i.e., a reference sample providing a low NF (such as <2%), or a NF of 0.

As mentioned above, cell lines expressing a controlled amount of target protein may be used as the reference, in particular as a positive reference.

As discussed above, the methods the third and fourth aspects may be adapted to a selected reference value, such as one of the reference values presented above, and the reference prognosis will in such case be a consequence of the selected reference value. As a non-limiting example, if an nuclear fraction of <2% (NF<2%) is used as the reference value, an associated reference prognosis may be derived from FIG. 1A (overall survival analyzed, tumors in all stages) by studying the "low" curve (dotted line). At a given time from diagnosis, the cumulative survival corresponding to the "low" curve may be read from the figure, e.g., 25% after 5 years (60 months), which results in a reference prognosis being a probability of five-year overall survival of 25%. Consequently, subjects having sample values which are equal to the reference value NF<2% have a probability of five-year overall survival of 25%.

However, the above reference prognoses are only provided as illustrative examples, and the skilled person understands that the usefulness of the methods according to the above aspects is not limited to any specific reference prognosis or prognosis measure.

As a fifth aspect of the present disclosure, there is provided a kit for carrying out the method according an embodiment of aspects three or four, which comprises:

a) an affinity ligand according to the first aspect; and
b) reagents necessary for quantifying the amount of said affinity ligand.

Various components, of the kit according to the sixth aspect may be selected and specified as described above in connection with the method aspects of the present disclosure. Consequently, the reagents may for example comprise a secondary affinity ligand as described above. Further, the kit may comprise one or more reference sample(s) for provision of the reference value. The wording "reference sample for the provision of the reference value" is to be interpreted broadly in the context of the present disclosure. The reference sample may comprise an amount of target protein actually corresponding to the reference value, but it may also comprise an amount of target protein corresponding to a value being higher than the reference value. In the latter case, the "high" value may be used by a person performing the method as an upper reference (positive reference) for assessing, e.g., the appearance of, a reference value which is lower than the "high" value. The person skilled in the art of immunohistochemistry understands how to do such an assessment. Further, as an alternative or a complementing example, the skilled person may use another reference sample comprising a low amount of target protein for provision of a "low" value in such an assessment, e.g., as a negative reference. This is further discussed above in connection with the method aspects. In embodiments of the kit aspect, the reference sample may be a tissue sample, such as a tissue sample adapted to ocular or microscopic evaluation. As an example, the tissue reference sample may be fixated in paraffin or buffered formalin and/or histo-processed to μm-thin sections that are mounted on microscopic glass-slides. The tissue reference sample may be further adapted to staining with affinity ligands, such as an affinity ligand according to the first aspect.

Thus, the kit according to the present disclosure comprises an affinity ligand according to the first aspect, as well as other means that help to quantify the affinity ligand after it has bound specifically and/or selectively to the target protein. For example, the kit may contain a secondary affinity ligand for detecting and/or quantifying a complex formed by the target protein and the affinity ligand in question. The kit may also contain various auxiliary substances other than affinity ligands, to enable the kit to be used easily and efficiently. Examples of auxiliary substances include solvents for dissolving or reconstituting lyophilized protein components of the kit, wash buffers, substrates for measuring enzyme activity in cases where an enzyme is used as a label, target retrieval solution to enhance the accessibility to antigens in cases where paraffin or formalin-fixed tissue samples are used, and substances such as reaction arresters, e.g., endogenous enzyme block solution to decrease the background staining and/or counterstaining solution to increase staining contrast, that are commonly used in immunoassay reagent kits.

As a sixth aspect of the present invention, there is provided an isolated polypeptide consisting of 47 acid residues or less and comprising the amino acid sequence of SEQ ID NO:1 and/or SEQ ID NO:2.

This sixth aspect of the present disclosure is based on, but not limited to, the inventors' insight of that certain epitopes are particularly interesting, e.g. for detecting expression of the target protein in various contexts, and that fragments comprising those epitopes may be utilized for production, selection or purification of diagnostic or prognostic means.

The different embodiments of the sixth aspect described below are discussed above in connection with the first aspect.

In embodiments of the sixth aspect, the polypeptide may comprise the amino acid sequence of SEQ ID NO:1. Further, in such embodiments, the polypeptide may comprise the amino acid sequence SEQ ID NO:3 and/or SEQ ID NO:4. Still further, in the embodiments wherein the polypeptide comprises the sequence SEQ ID NO:3, the polypeptide may comprise or consist of an amino acid sequence selected from the group consisting of SEQ ID NO:31-37. And in the embodiments wherein the polypeptide comprises the sequence SEQ ID NO:4, the polypeptide may comprise or consist of an amino acid sequence selected from the group consisting of SEQ ID NO:6-14.

Also, in embodiments of the sixth aspect, the polypeptide may comprise the amino acid sequence of SEQ ID NO:5. In such embodiments, the polypeptide may comprise or consist of an amino acid sequence selected from the group consisting of SEQ ID NO:52-59 and 78-82.

In embodiments of the sixth aspect, the polypeptide may consist of 45 amino acid residues or less, such as 43 amino acid residues or less, such as 42 amino acid residues or less, such as 41 amino acid residues or less, such as 39 amino acid residues or less, such as 38 amino acid residues or less, such as 37 amino acid residues or less, such as 34 amino acid residues or less, such as 33 amino acid residues or less, such as 31 amino acid residues or less.

Further in embodiments of the sixth aspect, the polypeptide may consist of 25 amino acid residues or less, such as 20 amino acid residues or less, such as 17 amino acid residues or less, such as 14 amino acid residues or less.

For example, the polypeptide of the sixth aspect may be used in an immunization, e.g., in the preparation of monoclonal or polyclonal antibodies.

Consequently, in embodiments of the sixth aspect, the polypeptide may be for use as an antigen in an immunization, e.g., in the preparation of a monoclonal or polyclonal antibodies.

Accordingly, there is provided, as a seventh aspect of the present disclosure, use of a polypeptide according to the sixth aspect as an antigen, e.g., in an immunization. For example, the immunization may be of a non-human animal. Similarly, there is provided a use of a polypeptide according to the sixth aspect in the preparation of an antibody, such as a monoclonal or polyclonal antibody.

Further, there is provided a use of a polypeptide according to the sixth aspect in the selection or purification of an affinity ligand. Such as an affinity ligand may for example be for establishing a prognosis for a mammalian subject having a colorectal cancer or another type of prognostic means. For example, such use may comprise affinity purification on a solid support onto which the polypeptide has been immobilized. The solid support may for example be arranged in a column. Further, the use may comprise selection of affinity ligands having specificity for a polypeptide according to the third aspect using a solid support onto which the polypeptide has been immobilized. Such solid support may be 96 well plates, magnetic beads, agarose beads or sepharose beads. Further, the use may comprise analysis of affinity ligands on a soluble matrix for example using a dextran matrix or use in a surface plasmon resonance instrument, such as a Biacore™ instrument, were the analysis may for example comprise monitoring the affinity for the immobilized polypeptide and a number of potential affinity ligands.

As an eighth aspect of the present disclosure, there is provided an affinity ligand capable of selective interaction with an epitope sequence consisting of 26 amino acids or less and comprising the amino acid sequence of SEQ ID NO:87, SEQ ID NO:105 and/or SEQ ID NO:106.

This eighth aspect of the present disclosure is based on that the inventors have identified certain epitopes (i.e. SEQ ID NO:87, SEQ ID NO:105 and/or SEQ ID NO:106) with which polyclonal antibodies generated against a SATB2 antigen (SEQ ID NO:111) interacts. Affinity ligands interacting with such epitopes may for example be used in various analyses, methods, assays or set-ups for establishing the prognosis for a subject having a colorectal cancer. In general in such applications, it is more desirable to have affinity ligands which are specific for a certain epitope than affinity ligands, such as polyclonal antibodies, that are only specific for a full-length protein or a longer fragment (such as an antigen) thereof. Further, the full length SATB2 protein and the antigen fragment thereof (SEQ ID NO:111) comprise several sequence parts which SATB1 protein and SATB2 protein have in common. In some cases, for example where they are both expressed, it may be desirable distinguish between the two proteins. SEQ ID NO:87, SEQ ID NO:105 and/or SEQ ID NO:106 are all unique to SATB2, and an affinity ligand capable of selective interaction with any of these may therefore meet such need.

A number of polypeptide fragments being of the defined length, i.e., SEQ ID NO:88-91, were used in the identification of SEQ ID NO:87. Consequently, in embodiments of the eighth aspect, the epitope sequence in question may comprise or consist of an amino acid sequence selected from the group consisting of SEQ ID NO:88-91.

Further, a number of other polypeptide fragments being of the defined length, i.e., SEQ ID NO:108-110, were used in the identification of SEQ ID NO:105. Consequently, in embodiments of the eighth aspect, the epitope sequence in question may comprise or consist of an amino acid sequence selected from the group consisting of SEQ ID NO:108-110.

The above-mentioned fragments are 25, 26, 22, 24 and 14 amino acids long, respectively.

Consequently, in embodiments of the eighth aspect, the epitope sequence in question may consist of 25 amino acid residues or less, such as 24 amino acid residues or less, such as 22 amino acid residues or less, such as 14 amino acid residues or less. In the epitope sequence according to the eighth aspect, the amino acids flanking SEQ ID NO:87, SEQ ID NO:105 or SEQ ID NO:106 may for example be those which are flanking them in the protein SATB2.

The various embodiments of affinity ligands according to the first aspect, such as their type and manufacture, applies mutatis mutandis to the affinity ligands of the eighth aspect.

So do also the uses of the second aspect. Thus, uses of the affinity ligand according to the eighth aspect constitutes a ninth aspect of the present disclosure.

Further, the affinity ligands according to eighth aspect may be used in a method corresponding to the third aspect. Thus, as a tenth aspect of the present disclosure, there is provided a method for determining whether a prognosis for a mammalian subject having a colorectal cancer is worse than or equal to a reference prognosis, comprising the steps of:
  a) providing a sample earlier obtained from said subject;
  b) evaluating the amount of SATB2 protein present in at least part of said sample using an affinity ligand according to the eighth aspect, and determining a sample value corresponding to said evaluated amount;
  c) comparing said sample value obtained in step d) with a reference value associated with said reference prognosis; and, if said sample value is lower than or equal to said reference value,
  d) concluding that said prognosis for said subject is worse than or equal to said reference prognosis.

Consequently, the SATB2 protein in the tenth aspect corresponds to the target protein in the third.

Also, the affinity ligands according to eighth aspect may be used in a method corresponding to the fourth aspect. Thus, as an eleventh aspect of the present disclosure, there is provided a method of treatment of a subject in need thereof, wherein said subject is having a colorectal cancer, comprising the steps of:
  a) providing a sample from said subject;
  b) evaluating the amount of SATB2 protein present in at least part of said sample using an affinity ligand according to the eighth aspect, and determining a sample value corresponding to said evaluated amount;
  c) comparing said sample value obtained in step d) with a reference value associated with said reference prognosis; and, if said sample value is lower than or equal to said reference value,
  d) treating said subject with an adjuvant colorectal cancer treatment regimen.

The various configurations and embodiments of the third and fourth aspect applies mutatis mutandis to the tenth and eleventh aspect, respectively.

As a twelfth aspect of the present disclosure, there is provided a kit for carrying out the method according an embodiment of aspects ten or eleven, which comprises:
  a) an affinity ligand according to the eighth aspect; and
  b) reagents necessary for quantifying the amount of said affinity ligand.

The various embodiments of the fifth aspect applies mutatis mutandis to the twelfth aspect.

As an thirteenth aspect of the present disclosure, there is provided a polypeptide consisting of 26 amino acids or less and comprising the amino acid sequence of SEQ ID NO:87, SEQ ID NO:105 and/or SEQ ID NO:106.

As mentioned above, a number of polypeptide fragments being of the defined length, i.e., SEQ ID NO:88-91, were used in the identification of SEQ ID NO:87. Consequently, in embodiments of the thirteenth aspect, the polypeptide in question may comprise or consist of an amino acid sequence selected from the group consisting of SEQ ID NO:88-91.

As also mentioned above, a number of other polypeptide fragments being of the defined length, i.e., SEQ ID NO:108-110, were used in the identification of SEQ ID NO:105. Consequently, in embodiments of the thirteenth aspect, the polypeptide in question may comprise or consist of an amino acid sequence selected from the group consisting of SEQ ID NO:108-110.

Finally, as also discussed above, the above-mentioned fragments are 25, 26, 22, 24 and 14 amino acids long, respectively.

Thus, in embodiments of the thirteenth aspect, the polypeptide in question consists of 25 amino acid residues or less, such as 24 amino acid residues or less, such as 22 amino acid residues or less, such as 14 amino acid residues or less. In the polypeptide according to the thirteenth aspect, the amino acids flanking SEQ ID NO:87, SEQ ID NO:105 or SEQ ID NO:106 may for example be those which are flanking them in the protein SATB2.

As a fourteenth aspect of the present disclosure, the are provided uses of the polypeptide according to the thirteenth aspect. The various embodiments of the seventh aspect applies mutatis mutandis to the fourteenth aspect.

EXAMPLES

1) Generation of Antigen
a. Materials and Methods

A suitable fragment of the target protein encoded by the EnsEMBL Gene ID ENSG00000119042 was designed using bioinformatic tools with the human genome sequence as template (Lindskog M et al (2005) Biotechniques 38:723-727, EnsEMBL, www.ensembl.org). A fragment consisting of 123 amino acids corresponding to amino acids 377-499 (SEQ ID NO:111) of the protein SATB2 (EnsEMBL entry no. ENSP00000260926) was designed. A polynucleotide encoding the target protein, which polynucleotide contained nucleotides 1542-1910 of the long SATB2 gene transcript (EnsEMBL entry no. ENST00000260926), was isolated by a Superscript™ One-Step RT-PCR amplification kit with Platinum® Taq (Invitrogen) and a human total RNA pool panel as template (Human Total RNA Panel IV, BD Biosciences Clontech). Flanking restriction sites Notl and Ascl were introduced into the fragment through the PCR amplification primers, to allow in-frame cloning into the expression vector (forward primer: GTGTCCCAAGCTGTCTTTG (SEQ ID NO: 112), reverse primer: CTTGGCCCTTTTCATCTCC (SEQ ID NO: 113)). The downstream primer was biotinylated to allow solid-phase cloning as previously described, and the resulting biotinylated PCR product was immobilized onto Dynabeads M280 Streptavidin (Dynal Biotech, Oslo, Norway) (Larsson M et al (2000) J. Biotechnol. 80:143-157). The fragment was released from the solid support by Notl-Ascl digestion (New England Biolabs), ligated into the pAff8c vector (Larsson M et al, supra) in frame with a dual affinity tag consisting of a hexahistidyl tag for immobilized metal ion chromatography (IMAC) purification and an immunopotentiating albumin binding protein (ABP) from streptococcal protein G (Sjolander A et a/(1997) J. Immunol. Methods 201 :115-123; Stahl S et al (1999) Encyclopedia of Bioprocess Technology: Fermentation, Biocatalysis and Bioseparation (Fleckinger MC and Drew SW, eds) John Wiley and Sons Inc., New York, pp 49-63), and transformed into *E. coli* BL21 (DE3) cells (Novagen). The sequences of the clones were verified by dye-terminator cycle sequencing of plasmid DNA amplified using TempliPhi DNA sequencing amplification kit (GE Healthcare, Uppsala, Sweden) according to the manufacturer's recommendations. 21(DE3) cells harboring the expression vector were inoculated in 100 ml 30 g/l tryptic soy broth (Merck KGaA) supplemented with 5 g/l yeast extract (Merck KGaA) and 50 mg/l kanamycin (Sigma-Aldrich, St-Louis) by addition of 1 ml of an overnight culture in the same culture medium. The cell culture was incubated in a 1 liter shake flask at 37° C. and 150 rpm until the optical density at 600 nm reached 0.5-1.5. Protein expression was then induced by addition of isopropyl-β-D-thiogalactopyranoside (Apollo Scientific) to a final concentration of 1 mM, and the incubation was continued overnight at 25° C. and 150 rpm. The cells were harvested by centrifugation at 2400 g, and the pellet was re-suspended in 5 ml lysis buffer (7 M guanidine hydrochloride, 47 mM $Na_2HPO_4$, 2.65 mM $NaH_2PO_4$, 10 mM Tris-HCl, 100 mM NaCl, 20 mM (3-mercaptoethanol; pH=8.0) and incubated for 2 hours at 37° C. and 150 rpm. After centrifugation at 35300 g, the supernatant containing the denatured and solubilized gene products was collected.

The $His_6$-tagged fusion protein was purified by immobilized metal ion affinity chromatography (IMAC) on columns with 1 ml Talon® metal ($CO^{2+}$) affinity resin (BD Biosciences Clontech) using an automated protein purification procedure (Steen J et al (2006) Protein Expr. Purif. 46:173-178) on an ASPEC XL4™ (Gilson). The resin was equilibrated with 20 ml denaturing washing buffer (6 M guanidine hydrochloride, 46.6 mM $Na_2HPO_4$, 3.4 mM $NaH_2PO_4$, 300 mM NaCl, pH 8.0-8.2) before the clarified cell lysate was loaded. The resin was then washed with a minimum of 31.5 ml washing buffer prior to elution in 2.5 ml elution buffer (6 M urea, 50 mM $NaH_2PO_4$, 100 mM NaCl, 30 mM acetic acid, 70 mM Na-acetate, pH 5.0). The eluted material was fractioned in three pools of 500, 700 and 1300 μl. The 700 μl fraction, here referred to as the antigen fraction, and the pooled 500 and 1300 μl fractions were stored for further use.

The antigen fraction was diluted to a final concentration of 1 M urea with phosphate buffered saline (PBS; 1.9 mM $NaH_2PO_4$, 8.1 mM $Na_2HPO_4$, 154 mM NaCl) followed by a concentration step to increase the protein concentration using Vivapore 10/20 ml concentrator with molecular weight cut off at 7500 Da (Vivascience AG). The protein concentration was determined using a bicinchoninic acid (BCA) micro assay protocol (Pierce) with a bovine serum albumin standard according to the manufacturer's recommendations. The protein quality was analyzed on a Bioanalyzer instrument using the Protein 50 or 200 assay (Agilent Technologies).
b. Results A gene fragment, corresponding to nucleotides 1542-1910 of the long transcript of the SATB2 gene and encoding a peptide (SEQ ID NO:111) consisting of amino acids 377 to 499 of the SATB2 protein was successfully isolated by RT-PCR from a human RNA pool using primers specific for the protein fragment. However, there was one single silent nucleotide mutation in the sequence compared to the sequence of ENSG00000119042 from EnsEMBL. The 123 amino acid fragment (SEQ ID NO:111) of the target protein was designed to lack transmembrane regions to ensure efficient expression in *E. coli*, and to lack any signal peptide, since those are cleaved off in the mature protein. In addition, the protein fragment was designed to be of a suitable size to allow the formation of conformational epitopes and still allow efficient cloning and expression in bacterial systems.

A clone encoding the correct amino acid sequence was identified, and, upon expression in *E. coli*, a single protein of the correct size was produced and subsequently purified using immobilized metal ion chromatography. After dilution of the antigen fraction to a final concentration of 1 M urea, the concentration of the protein fragment was determined to be 7.4 mg/ml and was 98% pure according to purity analysis.

2) Generation of Monoclonal Antibodies a) Materials and Methods

The purified fragment (SEQ ID NO:111) as obtained in Examples, section 1 was used as antigen for production of monoclonal antibodies. Antigen was sent to AbSea Biotechnology Ldt (Beijing, China) and briefly, the antigen was injected subcutaneously into BALB/c mice (4-6 weeks old, female) at three week intervals. The antigen was mixed with complete Freund's adjuvant for the first injection and incomplete Freund's adjuvant for the following injections. Three days before fusion, the mouse was last challenged with antigen intravenously. Hybridomas were generated by fusion of mouse splenocytes with the Sp2/0 myeloma cell line. By screening several cell lines using ELISA, cells that secreted antibodies specific for the antigen (SEQ ID NO:111) were identified and delivered to Atlas Antibodies AB for further characterization. Cell lines that showed positive results in ELISA, Western blot (WB) and immunohistochemistry (IHC) were selected for subcloning, performed by AbSea Biotechnology Ldt.

In addition, the immunohistochemical staining patterns of the monoclonal antibodies were compared to that of an in-house polyclonal anti-SATB2 antibody (HPA001042, Atlas Antibodies AB, Sweden; generated using the antigen SEQ ID NO:111). This antibody is sometimes referred to herein as the "HPA polyclonal antibody" or the "HPA msAb".

b) Results

Cell-lines were screened by ELISA (at AbSea) to identify lines that produce monoclonal antibodies (mAbs) that recognize the antigen (SEQ ID NO:111), but not the affinty tag His-ABP. Thirteen cell-lines showed specific binding to the antigen SEQ ID NO:111 in ELISA and were selected for further testing. For each of the selected thirteen clones 150-300 µl supernatant was collected, azide was added, and the supernatants were delivered to Atlas Antibodies AB on wet ice. The supernatants were stored at +4° C. upon arrival according to the instructions from AbSea. Further testing of the cell lines resulted in the identification of four cell lines (clones) (3B10, 8F11, 2B11 and 5E2) giving positive results in both Western blot and IHC analysis. These four clones were selected for subcloning and expansion, performed by AbSea Biotechnology Ldt.

Figure 6B:
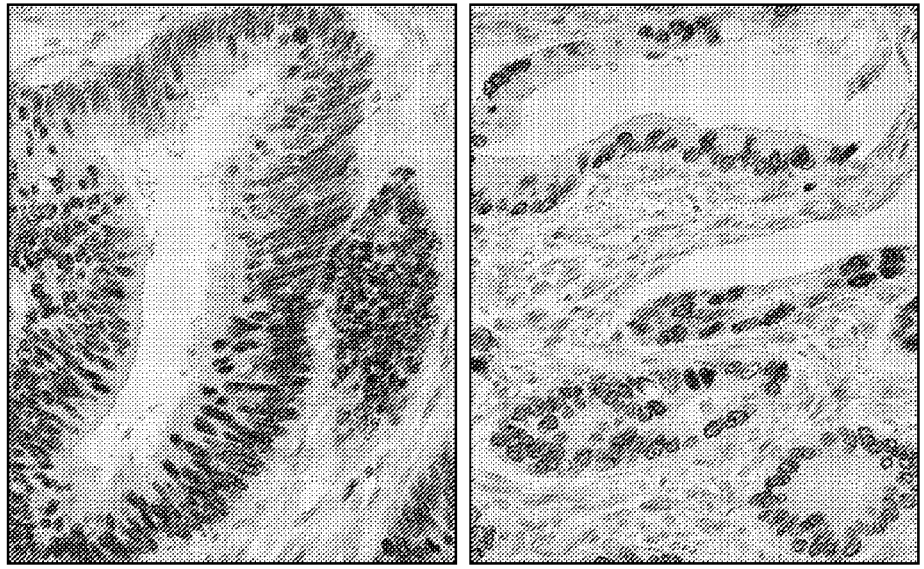
FIG. 6A shows the staining result using the polyclonal antibody HPA001042 (HPA msAB) and FIG. 6B shows the result of the monoclonal antibody 5E2.
Figure 6A:
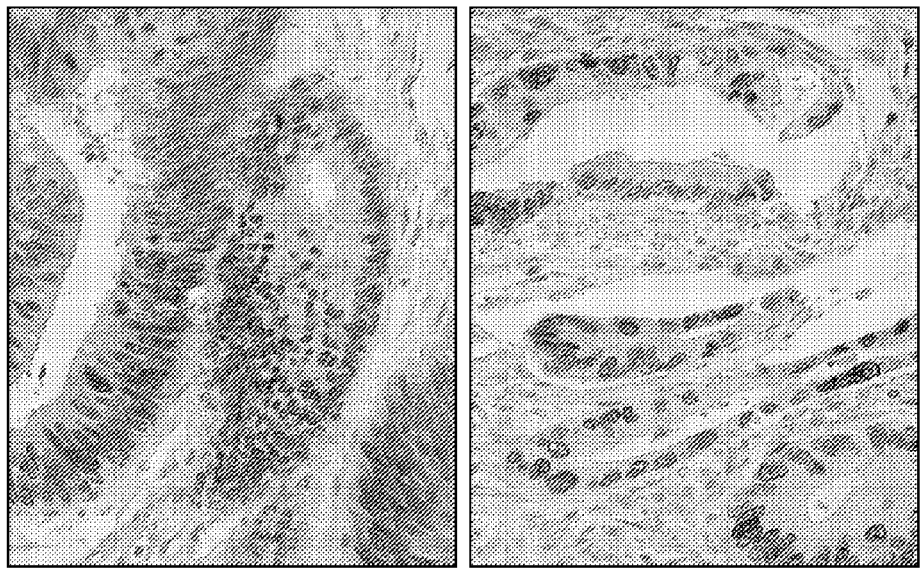
Figure 7B:
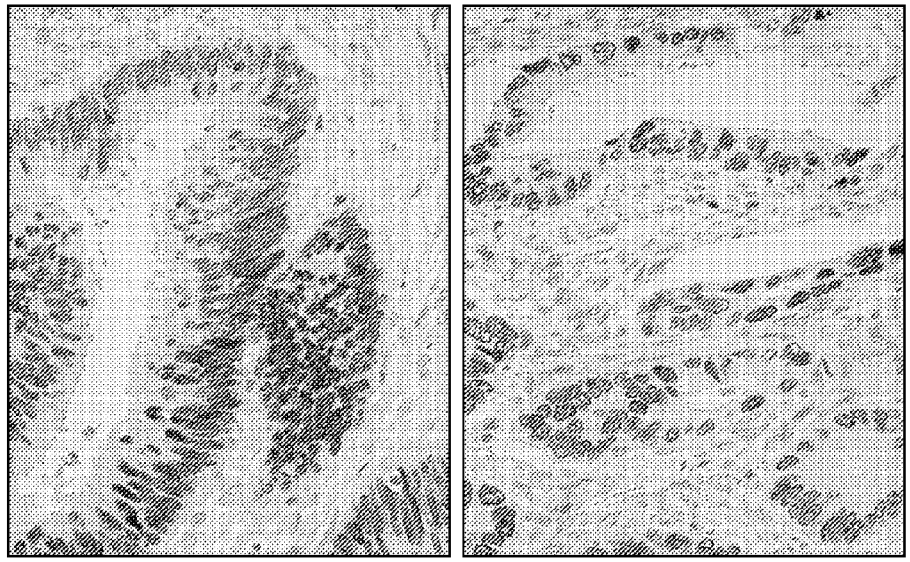
FIG. 7A shows the staining result using the polyclonal antibody HPA001042 (HPA msAB) and FIG. 7B shows the result of the monoclonal antibody 8F11.
Figure 7A:
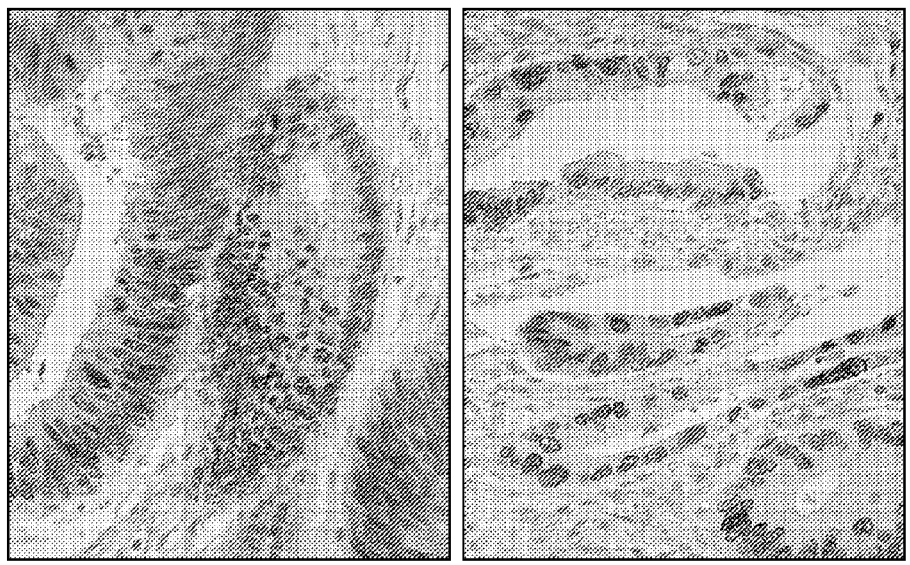

Immunohistochemical staining of colorectal carcinoma using the polyclonal antibody HPA001042 and the monoclonal antibodies 5E2 and 8F11 revealed nuclear staining of tumor cells for the tested antibodies. The monoclonal antibodies 5E2 and 8F11 yielded a more distinct and strong pattern as compared to the polyclonal antibody HPA001042 (FIGS. 6 and 7). Consequently, 5E2 and 8F11 are, at least in some aspects, more suitable for immunohistochemistry than the polyclonal antibody HPA001042.

3) Epitope Mapping Using Bacterial Display a) Subcloning of Libraries into the Staphylococcal Display Vector The *E. coli* strain RR1ΔM15 (Rüther, U. pUR 250 allows rapid chemical sequencing of both DNA strands of its inserts. Nucleic. Acids Res. 10, 5765-5772 (1982)) was used as host strain for plasmid constructions. A new staphylococcal vector, pSCEM1, was created by ligating a gene fragment containing a new restriction site (PmeI) to the previously described staphylococcal vector pSCXm (Wernérus, H. & Ståhl, S. Vector engineering to improve a staphylococcal surface display system. FEMS Microbiol Lett 212, 47-54 (2002)) digested with BamHI and SalI (New England Biolabs, Beverly, Mass.). Template for amplification of the SATB2 fragment gene was generously provided by Anja Persson (Royal institute of Technology, Stockholm; Sweden). The gene-fragment was amplified by PCR (9.6 ml, pooled) and sonicated (21% amplitude, constant sonication) using a microtip for 60 min in a 50 ml Falcon tube on ice in order to generate random fragments. Samples were thereafter concentrated by ultrafiltration using Centricon Plus 20 column (CO 10 kDa; Millipore, Billerica, Mass.). Concentrated fragments were blunt-ended and phosphorylated by addition of T4 DNA polymerase and T4 polynucleotide kinase (New England Biolabs) according to the supplier's recommendations. The blunt-ended gene fragments were thereafter ligated using T4 DNA Ligase (Invitrogen, Carlsbad, Calif.) into the staphylococcal display vector, pSCEM1, digested with PmeI (New England Biolabs). The library was transformed to electrocompetent *S. carnosus* TM300 (Götz, F. *Staphylococcus carnosus*: a new host organism for gene cloning and protein production. Soc. Appl. Bacteriol. Symp. Ser. 19, 49S-53S (1990)) as described previously (Löfblom, J., Kronqvist, N., Uhlén, M., Ståhl, S. & Wernérus, H. Optimization of electroporation-mediated transformation: *Staphylococcus carnosus* as model organism. J Appl Microbiol 102, 736-747 (2007)) and stored in 15% glycerol at −80° C.

b) Cell Labeling and Fluorescence-activated Cell Sorting (FACS)

An aliquot of Sc:SATB2-lib (at least ten times the library size) was inoculated to 100 ml TSB+Y (Tryptic soy broth+ yeast extract) with 20 µg ml$^{-1}$ chloramphenicol and grown over night at 37° C. and 150 rpm. After 16 hours, 10$^7$ cells were washed with 1 ml phosphate-buffered saline (PBS, pH 7.4) with 0.1% Pluronic® F108 NF Surfactant (PBSP; BASF Corporation, Mount Olive, N.J.). The cells were pelleted by centrifugation (3500×g, 4° C., 6 min) and resuspended in 100 µl PBSP containing antibody (i.e. the antibody used for epitope mapping; typically at a concentration around 100 nM) and incubated at room temperature with gentle mixing for 1 hour to reach equilibrium binding. The cells were thereafter washed with 1 ml of ice-cold PBSP followed by incubation in 1 ml PBSP containing 4 µg ml-1 Alexa Fluor® 488 goat anti-rabbit IgG (Invitrogen) or 4 µg ml-1 Alexa Fluor® 488 goat anti-mouse IgG (Invitrogen) and 225 nM Alexa Fluor® 647 HSA conjugate (Invitrogen) for 1 hour on ice in the dark. After a final washing step in 1 ml of ice-cold PBSP, the cells were resuspended in 300 µl of ice-cold PBSP before sorting. Cells were sorted using a FACSVantage SE (BD Biosciences, San Jose, Calif.) flow cytometer. The cells were sorted directly into 0.5 ml B2 medium (Löfblom, J., Kronqvist, N., Uhlén, M., Ståhl, S. & Wernérus, H. Optimization of electroporation-mediated transformation: *Staphylococcus carnosus* as model organism. J Appl Microbiol 102, 736-747 (2007)) and spread onto blood agar base (Merck) plates containing 10 µg ml-1 chloramphenicol and incubated at 37° C.

for 24 hours. In the last round, cells were sorted into individual wells in 96-well plates, containing semi-solid medium, to form colonies.

c) DNA Sequencing and BLAST Alignment

Parts of each colony were transferred to two separate wells in 96-well plates for PCR. The insert region of the staphylococcal display vector was amplified by PCR using two distinct primer pairs, yielding two PCR products containing a biotin molecule in the forward end and in the reverse end, respectively. Single stranded DNA was generated by NaOH strand separation of immobilized biotinylated PCR products on streptavidin-coated paramagnetic beads (Dynabeads M-270; Dynal Biotech, Oslo, Norway). Strand separation and annealing of pyrosequencing primer was performed using a Magnatrix 1200 pipetting robot (Magnetic Biosolutions AB, Stockholm, Sweden) in accordance with the manufacturer's instructions. A 10 cycles pyrosequencing at both ends of each insert was performed according to manufacturer's instructions using a PSQ™ 96 HS instrument (Biotage AB, Uppsala, Sweden). Complementary software was written in Perl for automatic analysis of pyrosequencing output files, including determination of reading frame, as well as BLAST alignment with the antigen.

d) Results

A SATB2 peptide library was constructed as described above and transformation yielded approximately 60,000 individual clones, resulting in an estimated 2,400 (4%) distinct functional antigen-derived fragments displayed on the staphylococcal surface. Flow cytometric sorting was carried out using a pool of polyclonal antibodies previously produced by means of an immunization using the antigen SEQ ID NO:111 (the polyclonal antibody HPA001042) and four monoclonal antibodies (3B10, 8F11, 2B11 and 5E2), all generated to the same antigen (SEQ ID NO:111). Positive cells were isolated in the second round of sorting after successful enrichment of antibody-binding cells. For the polyclonal antibody, two separate gates were used to collect cell populations with slightly different antibody-binding properties, while one gate was used for each of the monoclonal antibodies. Sequencing of the collected clones from each antibody-based sorting revealed five separate epitopes for the polyclonal antibody, while the binding patterns of all monoclonal antibodies demonstrated single binding epitopes. The identified consensus epitopes of the monoclonal antibodies (SEQ ID: 1 and 2) were found to be overlapping with two of the epitopes identified for the polyclonal antibody HPA001042 (sequences not included). These two epitopes were denoted epitope 1 (SEQ ID NO:1) and 2 (SEQ ID NO:2).

Based on sequencing information obtained using the monoclonal antibodies 8F11 and 5E2, the inventors found the consensus sequence for epitope 1 (SEQ ID NO:1, QNFLNLPE). Mapping of 8F11 revealed a 16 amino acid long epitope (SEQ ID NO:3, LRAMQNFLNLPEVERD) supported by SEQ ID NO: 31-51. In other words, the fragments SEQ ID NO: 31-51 were found to interact with 8F11 and the consensus sequence of SEQ ID NO:3 was identified. Regarding the monoclonal antibody 5E2, mapping revealed a 13 amino acid long epitope (SEQ ID NO:4, QNFLNLPEVERDI) supported by SEQ ID NO: 6-30. In other words, the fragments SEQ ID NO:6-30 were found to interact with 5E2 and the consensus sequence of SEQ ID NO:4 was identified.

Further, the inventors found the consensus sequence for epitope 2 (SEQ ID NO:2, GLLSEILRK) based on sequencing information obtained using the monoclonal antibodies 3B10 and 2B11. Mapping of 3B10 revealed a 10 amino acid long epitope (SEQ ID NO: 5, QGLLSEILRKE) supported by SEQ ID NO: 78-86. Regarding the monoclonal antibody 2B11, mapping revealed a 9 amino acid long epitop (SEQ ID NO:2, GLLSEILRK) supported by SEQ ID NO: 52-77.

Also, the inventors have identified three additional epitopes using the polyclonal antibody HPA001042, namely epitope 3 (SEQ ID NO:87) epitope 4 (SEQ ID NO:105) and epitope 5 (SEQ ID NO:106). The 12 amino acid epitope 3 (KTSTPTTDLPIK)(SEQ ID NO: 87) was identified by the inventors using mapping, and the epitope is a consensus sequence based on sequencing information from SEQ ID NO:88-104. Likewise, the 12 amino acid epitope 5 was identified by the inventors using mapping, and the epitope is a consensus sequence based on sequencing information from SEQ ID NO:107-110. Further, the 24 amino acid epitope 4 (VSSASSS PSSS RTPQAKTSTPTTD)(SEQ ID NO: 105) was also identified by the inventors using mapping.

4) Colon Carcinoma TMA (Sigmoid Cohort)

a) Material and Methods

Archival formalin-fixed paraffin-embedded tissue from 305 patients (148 women and 157 men) surgically treated for sigmoid cancer between 1993 and 2003 was collected from the Department of Pathology, Malmö University Hospital, Sweden. The median age of patients was 74 (39-97) years. 49 tumors were Dukes' stage A, 127 Dukes' stage B, 89 Dukes' stage C and 46 with Dukes' stage D. Information regarding the date of death was obtained from the regional cause-of-death registries for all patients. Ethical permission was obtained from the Local Ethics Committee.

All 305 cases were histopathologically re-evaluated on slides stained with hematoxylin and eosin. TMA:s were then constructed by sampling 2×1.0 mm cores per case from areas representative of sigmoid colon carcinoma.

Automated immunohistochemistry was performed as previously described (Kampf C et al (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, Dako, Copenhagen, Denmark) and boiled for 4 min at 125° C. in a Decloaking chamber® (Biocare Medical). Slides were placed in the Autostainer® (Dako) and endogenous peroxidase was initially blocked with $H_2O_2$ (Dako). The slides were incubated for 30 min at room temperature with the primary antibodies 5E2 and 8F11 obtained as in Examples, Section 2, followed by incubation for 30 min at room temperature with goat anti-rabbit peroxidase conjugated Envision®. Between all steps, slides were rinsed in wash buffer (Dako). Finally, diaminobenzidine (Dako) was used as chromogen and Harris hematoxylin (Sigma-Aldrich) was used for counterstaining. The slides were mounted with Pertex® (Histolab).

All samples of immunohistochemically stained tissue were manually evaluated under the microscope and annotated by a certified pathologist. Annotation of each sample was performed using a simplified scheme for classification of IHC outcome. Each tissue was examined for representativity and immunoreactivity. Both tumor cells and stroma were annotated. Basic annotation parameters included an evaluation of i) subcellular localization (nuclear and/or cytoplasmic/membranous), ii) staining intensity (SI) and iii) fraction of stained cells (FSC). Staining intensity was subjectively evaluated in accordance to standards used in clinical histo-pathological diagnostics and outcome was classified as: absent=no immunoreactivity, weak=faint immunoreactivity, moderate=medium immunoreactivity or strong=distinct and strong immunoreactivity. The skilled artisan will recognize that this procedure is similar to a calculation of an Allred score, see e.g. Allred et al (1998) Mod Pathol 11(2), 155.

For statistical analyses, the nuclear fraction (NF) and nuclear intensity (NI) level was evaluated. Both NF and NI was subjectively evaluated in accordance with standards used in clinical histopathological diagnostics: The "nuclear fraction" corresponded to the percentage of tumor cells in a sample that exhibits a positive staining in the nucleus, wherein a medium or distinct and strong immunoreactivity in the nucleus is considered positive and no or faint immunoreactivity in the nucleus is considered negative. The "nuclear intensity" corresponded to the overall staining intensity of the sample. However, only the expression of the nuclei of the cells was taken into account. Outcome of a nuclear intensity determination was classified as: absent=no overall immunoreactivity in the nuclei of tumor cells of the sample, weak=faint overall immunoreactivity in the nuclei of tumor cells of the sample, moderate=medium overall immunoreactivity in the nuclei of tumor cells of the sample, or strong=distinct and strong overall immunoreactivity in the nuclei of tumor cells of the sample. Based on the survival trends for individual strata, a dichotomized variable was constructed for further statistical analyses. For analysis using the 5E2 antibody, a high nuclear fraction (NF>0) was defined as 2-100% fraction of cells stained and a low nuclear fraction (NF=0) was defined as <2% fraction of cells stained. Further, a weak, moderate and strong nuclear intensity (NI>0) was defined as a high protein expression level and absent, nuclear intensity (NI=0) as a low protein expression level. The 8F11 antibody stained stronger and thus a high nuclear fraction (NF=1) was defined as >75% fraction of cells stained and a low nuclear fraction (NF<1) was defined as 0-75% fraction of cells stained. Further, a strong nuclear intensity (NI=1) was defined as a high protein expression and an absent, weak and moderate nuclear intensity (NI<1) as a low protein expression.

The above classification of samples was used for overall survival (OS) analysis according to the Kaplan-Meier method, and the log-rank test was used to compare survival in different strata. All statistical tests were two-sided, and p-values of <0.05% were considered significant. All calculations were made with the statistical package SPSS16.0 (SPSS Inc. Illinois, USA).

b) Results

Figure 1A:
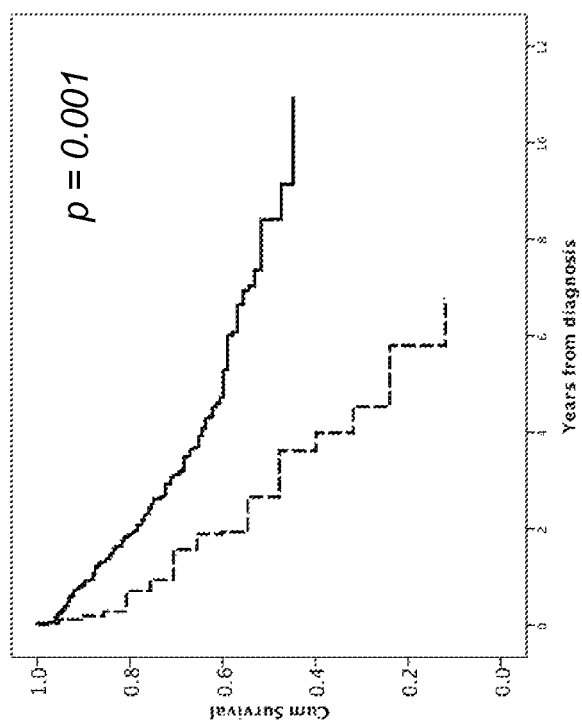
FIG. 1A, shows the result of all patients.
Figure 2B:
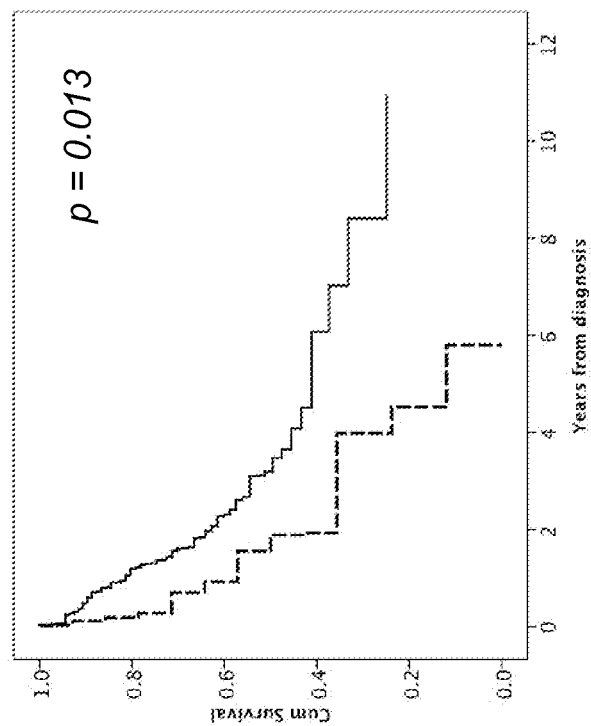
In FIG. 2B, only subjects with colorectal cancer in Duke's stage C or D were analyzed.
Figure 2A:
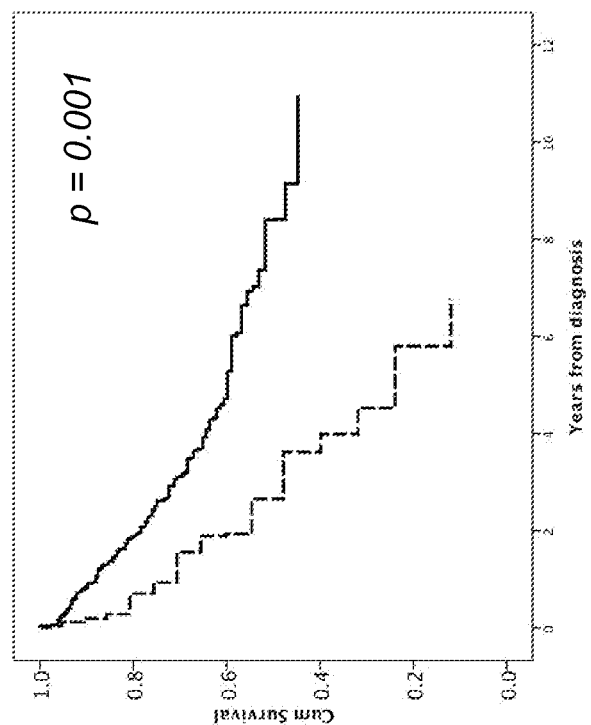
FIG. 2A, shows the result of all patients.

Tissue microarray based analysis of 305 sigmoid cancer patients showed that use of the monoclonal antibody 5E2 resulted in a strong and distinct nuclear staining where 261 subjects (86%) showed high expression (NF≧2%). Survival analysis based on the nuclear fraction for the entire cohort revealed a significantly (p=0.001) lower five year overall survival (OS) for patients having tumors with low expression of protein bound by 5E2 (FIG. 1A). About 60% of the patients having a high expression level are still alive after five years whereas only about 25% of the patients having a low expression level are alive after that time period. Further, when studying subjects diagnosed with Dukes' stage C and D, the difference in expected survival may be considered even more pronounced: about 40% of the patients having a high expression level in this subgroup are still alive after five years whereas as only 10% of the patients with a low protein expression level are after the same time period (p=0.01), see FIG. 1B. As a result of the cut-off used, the "low" category contained patients who had essentially lost their expression. Thus, loss of protein expression appears associated with a significantly worse prognosis, and this may be considered particularly pronounced at later stages of the disease, such as for patients diagnosed with Dukes' stage C and D. Similar results where obtained when studying nuclear intensity (FIGS. 2A and B).

Figure 3A:
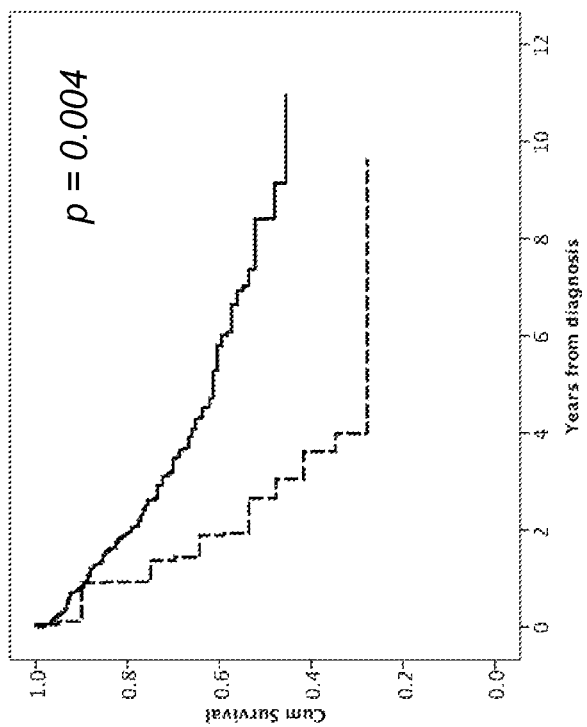
FIG. 3A, shows the result of all patients.
Figure 4A:
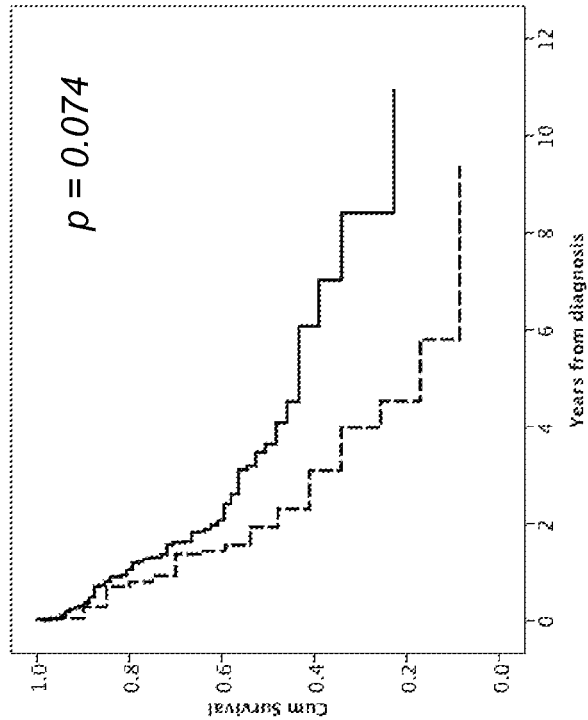
FIG. 4A, shows the result of all patients.
Figure 4B:
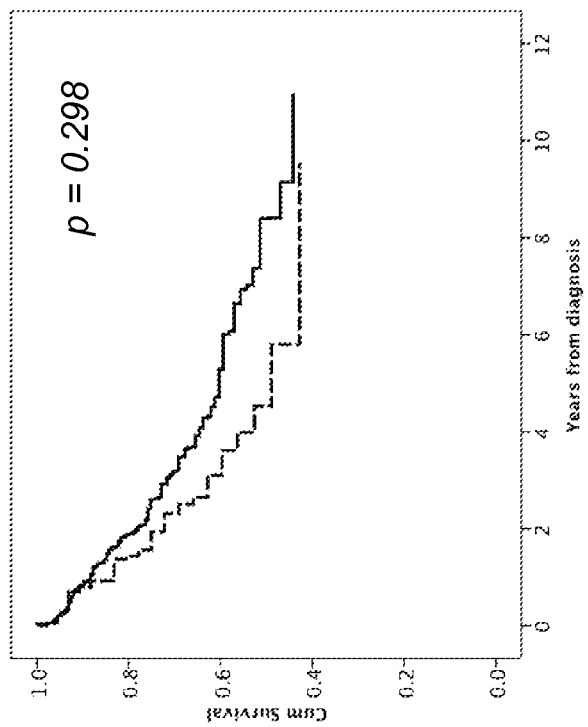
In FIG. 4B, only subjects with colorectal cancer in Duke's stage C or D were analyzed.

Tissue microarray based analysis of 305 sigmoid cancer patients showed that use of the monoclonal antibody 8F11 resulted in a strong and distinct nuclear staining where 275 subjects (90%) showed high expression (NF>75%). Survival analysis based on the nuclear fraction for the entire cohort revealed a significantly (p=0.004) shorter five year overall survival (OS) for patients having tumors with low protein expression (FIG. 3A). About 60% of the patients having a high protein level are still alive after five years whereas as only about 27% of the patients having a low expression level are alive after the same time period. Further, when studying subjects diagnosed with Dukes' stage C and D, the difference in expected survival may be considered even more pronounced. About 40% of the patients with a high protein level in this subgroup are still alive after five years whereas as only 12% of the patients with a low protein expression level are alive after the same time period, see FIG. 3B. Thus, a low level of protein expression is associated with a significantly worse prognosis, and that correlation may be considered to be even more pronounced at later stages of the disease, such as for patients diagnosed with Dukes' stage C and D. Similar results where obtained when studying nuclear intensity (FIGS. 4A and B).

In FIG. 5, the correlation in staining of 5E2 and 8F11 is analyzed. Nuclear fraction of stained tumor cells is compared by a crosstable, and reveals a significant (p=0.001) correlation between the two monoclonal antibodies. Consequently, this is in support of that the two monoclonal antibodies interact with the same epitope.

In conclusion, for a patient diagnosed with colorectal cancer, e.g. sigmoid carcinoma, the use of 5E2 and 8F11 may be of significant value for establishing a prognosis for a patient i.e. the probability of survival, such as five-year survival, as can be seen from FIGS. 1 to 4.

Establishment of a Prognosis for a Colorectal Cancer Patient

5. A Non-limiting Example

A cancer patient can present symptoms or signs from a tumor growth, focal symptoms including pain and distress from the region where the tumor grows or more general symptoms such as weight loss and fatigue. Signs from growth of a colorectal tumor can also become evident through blood in feces and/or dysfunction, e.g. diarrhea/constipation.

In the following, a monoclonal antibody (mAB) capable of selective interaction with the epitope sequence of SEQ ID NO:1 is employed. An example of such a monoclonal antibody is 5E2 obtained in Examples, section 2, above.

Following the establishment of a colorectal cancer diagnosis in a patient, a tumor tissue sample from the sigmoid colon is obtained. The tumor tissue sample may be obtained from a biopsy performed earlier during the diagnosis of the cancer or from a specimen from an earlier surgical removal of the tumor. Further, for the provision of a "negative reference", a sample is taken from archival material comprising tissue lacking detectable expression of protein comprising SEQ ID NO:1 (target protein). Such archival tissue may for example be colorectal cancer tissue previously shown to exhibit no expression when staining with the mAB. Further, for the provision of a "positive reference", a sample is taken from archival material comprising tissue having a pre-established high target protein expression. Such archival tissue may for example be colorectal cancer tissue previously shown to exhibit high expression, e.g., NF>75% or NI=strong, when staining with the mAB. The sample material is fixated in buffered formalin and histo-processed in order to obtain thin sections (4 μm) of the of the sample material.

Immunohistochemistry is performed as described in line with Examples, Section 4. One or more sample sections from each sample are mounted on glass slides that are incubated for 45 min in 60° C., de-paraffinized in xylene (2×15 min) and hydrated in graded alcohols. For antigen retrieval, slides are immersed in TRS (Target Retrieval Solution, pH 6.0, Dako) and boiled for 4 min at 125° C. in a Decloaking chamber® (Biocare Medical). Slides are placed in the Autostainer® (Dako) and endogenous peroxidase is initially blocked with H2O2 (Dako). The reason for mounting multiple sample sections may be to increase the accuracy of the results.

The mAB is added to the slides and incubated for 30 min in room temperature, followed by 30 min incubation in room temperature with a labeled secondary antibody; e.g. goat-anti-rabbit peroxidase conjugated Envision®. To detect the secondary antibody, diaminobenzidine (Dako) is used as chromogen, contrasted with a Harris hematoxylin (Sigma-Aldrich) counterstaining. Between all steps, slides are rinsed in wash buffer (Dako). The slides are then mounted with Pertex® (Histolab) mounting media.

As a tool to validate the staining procedure, two control cell-lines may be used; e.g. one slide with cells expressing the target protein (positive cell line) and one slide having cells having no target protein expression (negative cell line). The skilled artisan understands how to provide such cell lines, for example guided by the disclosure of Rhodes et al. (2006) The biomedical scientist, p 515-520. The control-line slides may be simultaneously stained in the same procedure as the colorectal cancer slides, i.e. incubated with the same primary and secondary antibodies.

For example, the sigmoid colon tumor tissue slide(s), the staining reference slides, and optionally, the slides with control cell-lines, may be scanned in a light microscope using a ScanScope T2 automated slide scanning system (Aperio Technologies) at ×20 magnification.

If control cell-lines are used, these are inspected to validate the staining procedure. If the cell-lines display staining results outside acceptable criteria, e.g. staining artifacts recognized by the skilled artisan, the staining of the biopsy samples is considered invalid and the whole staining procedure is repeated with new slides. If the positive and negative cell-lines display strong staining intensity and indistinct or no staining intensity, respectively, the staining is considered as valid.

The stained sample slide(s) from the tumor tissue biopsy is/are evaluated manually by visual inspection in accordance to standards used in clinical histo-pathological diagnostics, and the immunoreactivity of the colorectal tumor slide(s) is/are graded as in line with Examples, Section 4.

For example, the nuclear fraction (NF) may be determined. That is, the percentage of tumor cells in the sample slides that exhibit a positive staining in the nucleus is evaluated. A medium or distinct and strong immunoreactivity in the nucleus of a tumor cell is considered positive and no or faint immunoreactivity in the nucleus is considered negative. For example, a reference value of NF<2% may be used, and in such case, the sample(s) is/are divided into NF<2% or NF≧2%.

In the determination of the NF, the person performing the evaluation and grading is aided by visual inspection of the stained reference slides, i.e. the "positive reference" and the "negative reference".

The sample value(s), i.e. the NF(s), of the sample slide(s) from the tumor tissue is/are then compared to a reference value. If the sample value(s) is/are equal to or lower than the reference value, a conclusion is drawn that the prognosis is worse than or equal to a reference prognosis being associated with the reference value. As mentioned above, the reference value may be NF<2%. In such case, a reference prognosis being associated with that reference value may be derived from FIG. 1A. In FIG. 1A, NF<2% (dotted line) is associated with a probability of five-year overall survival of 25%. Consequently, if the sample value(s) of the patient in question is/are NF<2% (equal to the reference value), the prognosis for the patient is a probability of five-year overall survival of 25% (equal to the reference prognosis).

Generally

All cited material, including but not limited to publications, DNA or protein data entries, and patents, referred to in this application are herein incorporated by reference.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. A monoclonal antibody or Fab fragment, Fv fragment or scFv fragment of said antibody capable of selective interaction with an epitope sequence consisting of 17 amino acids or less, wherein said epitope sequence comprises the amino acid sequence of SEQ ID NO:1.

2. The monoclonal antibody or Fab fragment, Fv fragment or scFv fragment of said antibody according to claim 1, wherein said epitope sequence comprises the amino acid sequence SEQ ID NO:3 or SEQ ID NO:4.

3. The monoclonal antibody or Fab fragment, Fv fragment or scFv fragment of said antibody according to claim 1, which is a Fab fragment, Fv fragment or scFv fragment of said antibody.

4. The monoclonal antibody or Fab fragment, Fv fragment or scFv fragment of said antibody according to claim 1, which is a monoclonal antibody.

5. A kit, which comprises
   a) the monoclonal antibody or Fab fragment, Fv fragment or scFv fragment of said antibody according to claim 1; and
   b) reagents necessary for quantifying the amount of said affinity ligand.

6. A method of preparing the monoclonal antibody or Fab fragment, Fv fragment or scFv fragment of said antibody according to claim 1, comprising an immunization in which a polypeptide consisting of 17 amino acid residues or less and comprising the amino acid sequence of SEQ ID NO:1 is used as an antigen.

7. The method according to claim 6, further comprising selecting or purifying the monoclonal antibody or Fab fragment, Fv fragment or scFv fragment of said antibody by the method comprising contacting the monoclonal antibody or Fab fragment, Fv fragment or scFv fragment of said antibody with a polypeptide consisting of 17 amino acid residues or less and comprising the amino acid sequence of SEQ ID NO: 1.

* * * * *

SEQUENCE LISTING

```
<160> NUMBER OF SEQ ID NOS: 113

<210> SEQ ID NO 1
<211> LENGTH: 8
<212> TYPE: PRT
<213> ORGANISM: Homo sapiens

<400> SEQUENCE: 1

Gln Asn Phe Leu Asn Leu Pro Glu
1               5

<210> SEQ ID NO 2
<211> LENGTH: 9
<212> TYPE: PRT
<213> ORGANISM: Homo sapiens

<400> SEQUENCE: 2

Gly Leu Leu Ser Glu Ile Leu Arg Lys
```

<210> SEQ ID NO 3
<211> LENGTH: 16
<212> TYPE: PRT
<213> ORGANISM: Homo sapiens

<400> SEQUENCE: 3

Leu Arg Ala Met Gln Asn Phe Leu Asn Leu Pro Glu Val Glu Arg Asp
1               5                   10                  15

<210> SEQ ID NO 4
<211> LENGTH: 14
<212> TYPE: PRT
<213> ORGANISM: Homo sapiens

<400> SEQUENCE: 4

Gln Asn Phe Leu Asn Leu Pro Glu Val Glu Arg Asp Arg Ile
1               5                   10

<210> SEQ ID NO 5
<211> LENGTH: 11
<212> TYPE: PRT
<213> ORGANISM: Homo sapiens

<400> SEQUENCE: 5

Gln Gly Leu Leu Ser Glu Ile Leu Arg Lys Glu
1               5                   10

<210> SEQ ID NO 6
<211> LENGTH: 31
<212> TYPE: PRT
<213> ORGANISM: Homo sapiens

<400> SEQUENCE: 6

Gln Asn Phe Leu Asn Leu Pro Glu Val Glu Arg Asp Arg Ile Tyr Gln
1               5                   10                  15

Asp Glu Arg Glu Arg Ser Met Asn Pro Asn Val Ser Met Val Ser
            20                  25                  30

<210> SEQ ID NO 7
<211> LENGTH: 34
<212> TYPE: PRT
<213> ORGANISM: Homo sapiens

<400> SEQUENCE: 7

Ala Ser Gln Ser Leu Leu Val Asn Leu Arg Ala Met Gln Asn Phe Leu
1               5                   10                  15

Asn Leu Pro Glu Val Glu Arg Asp Arg Ile Tyr Gln Asp Glu Arg Glu
            20                  25                  30

Arg Ser

<210> SEQ ID NO 8
<211> LENGTH: 37
<212> TYPE: PRT
<213> ORGANISM: Homo sapiens

<400> SEQUENCE: 8

Glu Glu Asp Pro Arg Thr Ala Ser Gln Ser Leu Leu Val Asn Leu Arg
1               5                   10                  15

Ala Met Gln Asn Phe Leu Asn Leu Pro Glu Val Glu Arg Asp Arg Ile
            20                  25                  30

Tyr Gln Asp Glu Arg

-continued

35

<210> SEQ ID NO 9
<211> LENGTH: 38
<212> TYPE: PRT
<213> ORGANISM: Homo sapiens

<400> SEQUENCE: 9

Ala Ser Gln Ser Leu Leu Val Asn Leu Arg Ala Met Gln Asn Phe Leu
1               5                   10                  15

Asn Leu Pro Glu Val Glu Arg Asp Arg Ile Tyr Gln Asp Glu Arg Glu
            20                  25                  30

Arg Ser Met Asn Pro Asn
        35

<210> SEQ ID NO 10
<211> LENGTH: 41
<212> TYPE: PRT
<213> ORGANISM: Homo sapiens

<400> SEQUENCE: 10

Ala Ser Gln Ser Leu Leu Val Asn Leu Arg Ala Met Gln Asn Phe Leu
1               5                   10                  15

Asn Leu Pro Glu Val Glu Arg Asp Arg Ile Tyr Gln Asp Glu Arg Glu
            20                  25                  30

Arg Ser Met Asn Pro Asn Val Ser Met
        35                  40

<210> SEQ ID NO 11
<211> LENGTH: 42
<212> TYPE: PRT
<213> ORGANISM: Homo sapiens

<400> SEQUENCE: 11

Ala Ser Gln Ser Leu Leu Val Asn Leu Arg Ala Met Gln Asn Phe Leu
1               5                   10                  15

Asn Leu Pro Glu Val Glu Arg Asp Arg Ile Tyr Gln Asp Glu Arg Glu
            20                  25                  30

Arg Ser Met Asn Pro Asn Val Ser Met Val
        35                  40

<210> SEQ ID NO 12
<211> LENGTH: 43
<212> TYPE: PRT
<213> ORGANISM: Homo sapiens

<400> SEQUENCE: 12

Ala Ser Gln Ser Leu Leu Val Asn Leu Arg Ala Met Gln Asn Phe Leu
1               5                   10                  15

Asn Leu Pro Glu Val Glu Arg Asp Arg Ile Tyr Gln Asp Glu Arg Glu
            20                  25                  30

Arg Ser Met Asn Pro Asn Val Ser Met Val Ser
        35                  40

<210> SEQ ID NO 13
<211> LENGTH: 45
<212> TYPE: PRT
<213> ORGANISM: Homo sapiens

<400> SEQUENCE: 13

Glu Asp Pro Arg Thr Ala Ser Gln Ser Leu Leu Val Asn Leu Arg Ala
1               5                   10                  15

Met Gln Asn Phe Leu Asn Leu Pro Glu Val Glu Arg Asp Arg Ile Tyr
                20                  25                  30

Gln Asp Glu Arg Glu Arg Ser Met Asn Pro Asn Val Ser
            35                  40                  45

<210> SEQ ID NO 14
<211> LENGTH: 47
<212> TYPE: PRT
<213> ORGANISM: Homo sapiens

<400> SEQUENCE: 14

Ala Phe Asn Arg Thr Gln Gly Leu Leu Ser Glu Ile Leu Arg Lys Glu
1               5                   10                  15

Glu Asp Pro Arg Thr Ala Ser Gln Ser Leu Leu Val Asn Leu Arg Ala
                20                  25                  30

Met Gln Asn Phe Leu Asn Leu Pro Glu Val Glu Arg Asp Arg Ile
            35                  40                  45

<210> SEQ ID NO 15
<211> LENGTH: 49
<212> TYPE: PRT
<213> ORGANISM: Homo sapiens

<400> SEQUENCE: 15

Val Ala Phe Asn Arg Thr Gln Gly Leu Leu Ser Glu Ile Leu Arg Lys
1               5                   10                  15

Glu Glu Asp Pro Arg Thr Ala Ser Gln Ser Leu Leu Val Asn Leu Arg
                20                  25                  30

Ala Met Gln Asn Phe Leu Asn Leu Pro Glu Val Glu Arg Asp Arg Ile
            35                  40                  45

Tyr

<210> SEQ ID NO 16
<211> LENGTH: 49
<212> TYPE: PRT
<213> ORGANISM: Homo sapiens

<400> SEQUENCE: 16

Lys Glu Glu Asp Pro Arg Thr Ala Ser Gln Ser Leu Leu Val Asn Leu
1               5                   10                  15

Arg Ala Met Gln Asn Phe Leu Asn Leu Pro Glu Val Glu Arg Asp Arg
                20                  25                  30

Ile Tyr Gln Asp Glu Arg Glu Arg Ser Met Asn Pro Asn Val Ser Met
            35                  40                  45

Val

<210> SEQ ID NO 17
<211> LENGTH: 50
<212> TYPE: PRT
<213> ORGANISM: Homo sapiens

<400> SEQUENCE: 17

Leu Leu Ser Glu Ile Leu Arg Lys Glu Glu Asp Pro Arg Thr Ala Ser
1               5                   10                  15

Gln Ser Leu Leu Val Asn Leu Arg Ala Met Gln Asn Phe Leu Asn Leu
                20                  25                  30

Pro Glu Val Glu Arg Asp Arg Ile Tyr Gln Asp Glu Arg Glu Arg Ser
            35                  40                  45

Met Asn

<210> SEQ ID NO 18
<211> LENGTH: 51
<212> TYPE: PRT
<213> ORGANISM: Homo sapiens

<400> SEQUENCE: 18

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu
        35                  40                  45

Pro Glu Val
    50

<210> SEQ ID NO 19
<211> LENGTH: 52
<212> TYPE: PRT
<213> ORGANISM: Homo sapiens

<400> SEQUENCE: 19

Gln Gly Leu Leu Ser Glu Ile Leu Arg Lys Glu Glu Asp Pro Arg Thr
1               5                   10                  15

Ala Ser Gln Ser Leu Leu Val Asn Leu Arg Ala Met Gln Asn Phe Leu
            20                  25                  30

Asn Leu Pro Glu Val Glu Arg Asp Arg Ile Tyr Gln Asp Glu Arg Glu
        35                  40                  45

Arg Ser Met Asn
    50

<210> SEQ ID NO 20
<211> LENGTH: 55
<212> TYPE: PRT
<213> ORGANISM: Homo sapiens

<400> SEQUENCE: 20

Gln Asn Phe Leu Asn Leu Pro Glu Val Glu Arg Asp Arg Ile Tyr Gln
1               5                   10                  15

Asp Glu Arg Glu Arg Ser Met Asn Pro Asn Val Ser Met Val Ser Ser
            20                  25                  30

Ala Ser Ser Ser Pro Ser Ser Ser Arg Thr Pro Gln Ala Lys Thr Ser
        35                  40                  45

Thr Pro Thr Thr Asp Leu Pro
    50                  55

<210> SEQ ID NO 21
<211> LENGTH: 56
<212> TYPE: PRT
<213> ORGANISM: Homo sapiens

<400> SEQUENCE: 21

Leu Ser Glu Ile Leu Arg Lys Glu Glu Asp Pro Arg Thr Ala Ser Gln
1               5                   10                  15

Ser Leu Leu Val Asn Leu Arg Ala Met Gln Asn Phe Leu Asn Leu Pro
            20                  25                  30

Glu Val Glu Arg Asp Arg Ile Tyr Gln Asp Glu Arg Glu Arg Ser Met
        35                  40                  45

Asn Pro Asn Val Ser Met Val Ser

```
                50                  55

<210> SEQ ID NO 22
<211> LENGTH: 64
<212> TYPE: PRT
<213> ORGANISM: Homo sapiens

<400> SEQUENCE: 22

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu
        35                  40                  45

Pro Glu Val Glu Arg Asp Arg Ile Tyr Gln Asp Glu Arg Glu Arg Ser
    50                  55                  60

<210> SEQ ID NO 23
<211> LENGTH: 68
<212> TYPE: PRT
<213> ORGANISM: Homo sapiens

<400> SEQUENCE: 23

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu
        35                  40                  45

Pro Glu Val Glu Arg Asp Arg Ile Tyr Gln Asp Glu Arg Glu Arg Ser
    50                  55                  60

Met Asn Pro Asn
65

<210> SEQ ID NO 24
<211> LENGTH: 68
<212> TYPE: PRT
<213> ORGANISM: Homo sapiens

<400> SEQUENCE: 24

Gln Ser Leu Leu Val Asn Leu Arg Ala Met Gln Asn Phe Leu Asn Leu
1               5                   10                  15

Pro Glu Val Glu Arg Asp Arg Ile Tyr Gln Asp Glu Arg Glu Arg Ser
            20                  25                  30

Met Asn Pro Asn Val Ser Met Val Ser Ser Ala Ser Ser Pro Ser
        35                  40                  45

Ser Ser Arg Thr Pro Gln Ala Lys Thr Ser Thr Pro Thr Thr Asp Leu
    50                  55                  60

Pro Ile Lys Val
65

<210> SEQ ID NO 25
<211> LENGTH: 88
<212> TYPE: PRT
<213> ORGANISM: Homo sapiens

<400> SEQUENCE: 25

Thr Gln Gly Leu Leu Ser Glu Ile Leu Arg Lys Glu Glu Asp Pro Arg
1               5                   10                  15

Thr Ala Ser Gln Ser Leu Leu Val Asn Leu Arg Ala Met Gln Asn Phe
```

-continued

```
                    20                  25                  30
Leu Asn Leu Pro Glu Val Glu Arg Asp Arg Ile Tyr Gln Asp Glu Arg
            35                  40                  45
Glu Arg Ser Met Asn Pro Asn Val Ser Met Val Ser Ser Ala Ser Ser
        50                  55                  60
Ser Pro Ser Ser Ser Arg Thr Pro Gln Ala Lys Thr Ser Thr Pro Thr
65                  70                  75                  80
Thr Asp Leu Pro Ile Lys Val Asp
                85

<210> SEQ ID NO 26
<211> LENGTH: 90
<212> TYPE: PRT
<213> ORGANISM: Homo sapiens

<400> SEQUENCE: 26

Val Ser Gln Ala Val Phe Ala Arg Val Ala Phe Asn Arg Thr Gln Gly
1               5                   10                  15
Leu Leu Ser Glu Ile Leu Arg Lys Glu Glu Asp Pro Arg Thr Ala Ser
            20                  25                  30
Gln Ser Leu Leu Val Asn Leu Arg Ala Met Gln Asn Phe Leu Asn Leu
        35                  40                  45
Pro Glu Val Glu Arg Asp Arg Ile Tyr Gln Asp Glu Arg Glu Arg Ser
    50                  55                  60
Met Asn Pro Asn Val Ser Met Val Ser Ser Ala Ser Ser Ser Pro Ser
65                  70                  75                  80
Ser Ser Arg Thr Pro Gln Ala Lys Thr Ser
            85                  90

<210> SEQ ID NO 27
<211> LENGTH: 91
<212> TYPE: PRT
<213> ORGANISM: Homo sapiens

<400> SEQUENCE: 27

Gln Ser Leu Leu Val Asn Leu Arg Ala Met Gln Asn Phe Leu Asn Leu
1               5                   10                  15
Pro Glu Val Glu Arg Asp Arg Ile Tyr Gln Asp Glu Arg Glu Arg Ser
            20                  25                  30
Met Asn Pro Asn Val Ser Met Val Ser Ser Ala Ser Ser Ser Pro Ser
        35                  40                  45
Ser Ser Arg Thr Pro Gln Ala Lys Thr Ser Thr Pro Thr Thr Asp Leu
    50                  55                  60
Pro Ile Lys Val Asp Gly Ala Asn Ile Asn Ile Thr Ala Ala Ile Tyr
65                  70                  75                  80
Asp Glu Ile Gln Gln Glu Met Lys Arg Ala Lys
            85                  90

<210> SEQ ID NO 28
<211> LENGTH: 96
<212> TYPE: PRT
<213> ORGANISM: Homo sapiens

<400> SEQUENCE: 28

Val Ser Gln Ala Val Phe Ala Arg Val Ala Phe Asn Arg Thr Gln Gly
1               5                   10                  15
Leu Leu Ser Glu Ile Leu Arg Lys Glu Glu Asp Pro Arg Thr Ala Ser
            20                  25                  30
```

```
Gln Ser Leu Leu Val Asn Leu Arg Ala Met Gln Asn Phe Leu Asn Leu
            35                  40                  45

Pro Glu Val Glu Arg Asp Arg Ile Tyr Gln Asp Glu Arg Glu Arg Ser
        50                  55                  60

Met Asn Pro Asn Val Ser Met Val Ser Ser Ala Ser Ser Ser Pro Ser
 65                  70                  75                  80

Ser Ser Arg Thr Pro Gln Ala Lys Thr Ser Thr Pro Thr Thr Asp Leu
                85                  90                  95

<210> SEQ ID NO 29
<211> LENGTH: 114
<212> TYPE: PRT
<213> ORGANISM: Homo sapiens

<400> SEQUENCE: 29

Val Ser Gln Ala Val Phe Ala Arg Val Ala Phe Asn Arg Thr Gln Gly
 1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu
            35                  40                  45

Pro Glu Val Glu Arg Asp Arg Ile Tyr Gln Asp Glu Arg Glu Arg Ser
        50                  55                  60

Met Asn Pro Asn Val Ser Met Val Ser Ser Ala Ser Ser Ser Pro Ser
 65                  70                  75                  80

Ser Ser Arg Thr Pro Gln Ala Lys Thr Ser Thr Pro Thr Thr Asp Leu
                85                  90                  95

Pro Ile Lys Val Asp Gly Ala Asn Ile Asn Ile Thr Ala Ala Ile Tyr
            100                 105                 110

Asp Glu

<210> SEQ ID NO 30
<211> LENGTH: 123
<212> TYPE: PRT
<213> ORGANISM: Homo sapiens

<400> SEQUENCE: 30

Val Ser Gln Ala Val Phe Ala Arg Val Ala Phe Asn Arg Thr Gln Gly
 1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu
            35                  40                  45

Pro Glu Val Glu Arg Asp Arg Ile Tyr Gln Asp Glu Arg Glu Arg Ser
        50                  55                  60

Met Asn Pro Asn Val Ser Met Val Ser Ser Ala Ser Ser Ser Pro Ser
 65                  70                  75                  80

Ser Ser Arg Thr Pro Gln Ala Lys Thr Ser Thr Pro Thr Thr Asp Leu
                85                  90                  95

Pro Ile Lys Val Asp Gly Ala Asn Ile Asn Ile Thr Ala Ala Ile Tyr
            100                 105                 110

Asp Glu Ile Gln Gln Glu Met Lys Arg Ala Lys
            115                 120

<210> SEQ ID NO 31
<211> LENGTH: 33
<212> TYPE: PRT
<213> ORGANISM: Homo sapiens
```

<400> SEQUENCE: 31

Leu Arg Lys Glu Glu Asp Pro Arg Thr Ala Ser Gln Ser Leu Leu Val
1               5                   10                  15

Asn Leu Arg Ala Met Gln Asn Phe Leu Asn Leu Pro Glu Val Glu Arg
                20                  25                  30

Asp

<210> SEQ ID NO 32
<211> LENGTH: 38
<212> TYPE: PRT
<213> ORGANISM: Homo sapiens

<400> SEQUENCE: 32

Leu Val Asn Leu Arg Ala Met Gln Asn Phe Leu Asn Leu Pro Glu Val
1               5                   10                  15

Glu Arg Asp Arg Ile Tyr Gln Asp Glu Arg Glu Arg Ser Met Asn Pro
                20                  25                  30

Asn Val Ser Met Val Ser
                35

<210> SEQ ID NO 33
<211> LENGTH: 39
<212> TYPE: PRT
<213> ORGANISM: Homo sapiens

<400> SEQUENCE: 33

Glu Glu Asp Pro Arg Thr Ala Ser Gln Ser Leu Leu Val Asn Leu Arg
1               5                   10                  15

Ala Met Gln Asn Phe Leu Asn Leu Pro Glu Val Glu Arg Asp Arg Ile
                20                  25                  30

Tyr Gln Asp Glu Arg Glu Arg
                35

<210> SEQ ID NO 34
<211> LENGTH: 42
<212> TYPE: PRT
<213> ORGANISM: Homo sapiens

<400> SEQUENCE: 34

Ser Gln Ser Leu Leu Val Asn Leu Arg Ala Met Gln Asn Phe Leu Asn
1               5                   10                  15

Leu Pro Glu Val Glu Arg Asp Arg Ile Tyr Gln Asp Glu Arg Glu Arg
                20                  25                  30

Ser Met Asn Pro Asn Val Ser Met Val Ser
                35                  40

<210> SEQ ID NO 35
<211> LENGTH: 43
<212> TYPE: PRT
<213> ORGANISM: Homo sapiens

<400> SEQUENCE: 35

Ser Gln Ser Leu Leu Val Asn Leu Arg Ala Met Gln Asn Phe Leu Asn
1               5                   10                  15

Leu Pro Glu Val Glu Arg Asp Arg Ile Tyr Gln Asp Glu Arg Glu Arg
                20                  25                  30

Ser Met Asn Pro Asn Val Ser Met Val Ser Ser
                35                  40

<210> SEQ ID NO 36
<211> LENGTH: 45
<212> TYPE: PRT
<213> ORGANISM: Homo sapiens

<400> SEQUENCE: 36

Ala Ser Gln Ser Leu Leu Val Asn Leu Arg Ala Met Gln Asn Phe Leu
1               5                   10                  15

Asn Leu Pro Glu Val Glu Arg Asp Arg Ile Tyr Gln Asp Glu Arg Glu
            20                  25                  30

Arg Ser Met Asn Pro Asn Val Ser Met Val Ser Ser Ala
        35                  40                  45

<210> SEQ ID NO 37
<211> LENGTH: 47
<212> TYPE: PRT
<213> ORGANISM: Homo sapiens

<400> SEQUENCE: 37

Gly Leu Leu Ser Glu Ile Leu Arg Lys Glu Glu Asp Pro Arg Thr Ala
1               5                   10                  15

Ser Gln Ser Leu Leu Val Asn Leu Arg Ala Met Gln Asn Phe Leu Asn
            20                  25                  30

Leu Pro Glu Val Glu Arg Asp Arg Ile Tyr Gln Asp Glu Arg Glu
        35                  40                  45

<210> SEQ ID NO 38
<211> LENGTH: 49
<212> TYPE: PRT
<213> ORGANISM: Homo sapiens

<400> SEQUENCE: 38

Val Ala Phe Asn Arg Thr Gln Gly Leu Leu Ser Glu Ile Leu Arg Lys
1               5                   10                  15

Glu Glu Asp Pro Arg Thr Ala Ser Gln Ser Leu Leu Val Asn Leu Arg
            20                  25                  30

Ala Met Gln Asn Phe Leu Asn Leu Pro Glu Val Glu Arg Asp Arg Ile
        35                  40                  45

Tyr

<210> SEQ ID NO 39
<211> LENGTH: 53
<212> TYPE: PRT
<213> ORGANISM: Homo sapiens

<400> SEQUENCE: 39

Gly Leu Leu Ser Glu Ile Leu Arg Lys Glu Glu Asp Pro Arg Thr Ala
1               5                   10                  15

Ser Gln Ser Leu Leu Val Asn Leu Arg Ala Met Gln Asn Phe Leu Asn
            20                  25                  30

Leu Pro Glu Val Glu Arg Asp Arg Ile Tyr Gln Asp Glu Arg Glu Arg
        35                  40                  45

Ser Met Asn Pro Asn
    50

<210> SEQ ID NO 40
<211> LENGTH: 54
<212> TYPE: PRT
<213> ORGANISM: Homo sapiens

<400> SEQUENCE: 40

Arg Thr Ala Ser Gln Ser Leu Leu Val Asn Leu Arg Ala Met Gln Asn
1               5                   10                  15

Phe Leu Asn Leu Pro Glu Val Glu Arg Asp Arg Ile Tyr Gln Asp Glu
                20                  25                  30

Arg Glu Arg Ser Met Asn Pro Asn Val Ser Met Val Ser Ser Ala Ser
            35                  40                  45

Ser Ser Pro Ser Ser Ser
    50

<210> SEQ ID NO 41
<211> LENGTH: 63
<212> TYPE: PRT
<213> ORGANISM: Homo sapiens

<400> SEQUENCE: 41

Leu Val Asn Leu Arg Ala Met Gln Asn Phe Leu Asn Leu Pro Glu Val
1               5                   10                  15

Glu Arg Asp Arg Ile Tyr Gln Asp Glu Arg Glu Arg Ser Met Asn Pro
                20                  25                  30

Asn Val Ser Met Val Ser Ser Ala Ser Ser Ser Pro Ser Ser Ser Arg
            35                  40                  45

Thr Pro Gln Ala Lys Thr Ser Thr Pro Thr Thr Asp Leu Pro Ile
    50                  55                  60

<210> SEQ ID NO 42
<211> LENGTH: 64
<212> TYPE: PRT
<213> ORGANISM: Homo sapiens

<400> SEQUENCE: 42

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
                20                  25                  30

Asn Phe Leu Asn Leu Pro Glu Val Glu Arg Asp Arg Ile Tyr Gln Asp
            35                  40                  45

Glu Arg Glu Arg Ser Met Asn Pro Asn Val Ser Met Val Ser Ser Ala
    50                  55                  60

<210> SEQ ID NO 43
<211> LENGTH: 65
<212> TYPE: PRT
<213> ORGANISM: Homo sapiens

<400> SEQUENCE: 43

Leu Val Asn Leu Arg Ala Met Gln Asn Phe Leu Asn Leu Pro Glu Val
1               5                   10                  15

Glu Arg Asp Arg Ile Tyr Gln Asp Glu Arg Glu Arg Ser Met Asn Pro
                20                  25                  30

Asn Val Ser Met Val Ser Ser Ala Ser Ser Ser Pro Ser Ser Ser Arg
            35                  40                  45

Thr Pro Gln Ala Lys Thr Ser Thr Pro Thr Thr Asp Leu Pro Ile Lys
    50                  55                  60

Val
65

<210> SEQ ID NO 44
<211> LENGTH: 65
<212> TYPE: PRT
<213> ORGANISM: Homo sapiens

<400> SEQUENCE: 44

| Val | Ala | Phe | Asn | Arg | Thr | Gln | Gly | Leu | Leu | Ser | Glu | Ile | Leu | Arg | Lys |
|---|---|---|---|---|---|---|---|---|---|---|---|---|---|---|---|
| 1 | | | | 5 | | | | | 10 | | | | | 15 | |

Glu Glu Asp Pro Arg Thr Ala Ser Gln Ser Leu Leu Val Asn Leu Arg
            20                  25                  30

Ala Met Gln Asn Phe Leu Asn Leu Pro Glu Val Glu Arg Asp Arg Ile
        35                  40                  45

Tyr Gln Asp Glu Arg Glu Arg Ser Met Asn Pro Asn Val Ser Met Val
    50                  55                  60

Ser
65

<210> SEQ ID NO 45
<211> LENGTH: 66
<212> TYPE: PRT
<213> ORGANISM: Homo sapiens

<400> SEQUENCE: 45

Gln Ser Leu Leu Val Asn Leu Arg Ala Met Gln Asn Phe Leu Asn Leu
1               5                   10                  15

Pro Glu Val Glu Arg Asp Arg Ile Tyr Gln Asp Glu Arg Glu Arg Ser
            20                  25                  30

Met Asn Pro Asn Val Ser Met Val Ser Ser Ala Ser Ser Pro Ser
        35                  40                  45

Ser Ser Arg Thr Pro Gln Ala Lys Thr Ser Thr Pro Thr Thr Asp Leu
    50                  55                  60

Pro Ile
65

<210> SEQ ID NO 46
<211> LENGTH: 68
<212> TYPE: PRT
<213> ORGANISM: Homo sapiens

<400> SEQUENCE: 46

Arg Val Ala Phe Asn Arg Thr Gln Gly Leu Leu Ser Glu Ile Leu Arg
1               5                   10                  15

Lys Glu Glu Asp Pro Arg Thr Ala Ser Gln Ser Leu Leu Val Asn Leu
            20                  25                  30

Arg Ala Met Gln Asn Phe Leu Asn Leu Pro Glu Val Glu Arg Asp Arg
        35                  40                  45

Ile Tyr Gln Asp Glu Arg Glu Arg Ser Met Asn Pro Asn Val Ser Met
    50                  55                  60

Val Ser Ser Ala
65

<210> SEQ ID NO 47
<211> LENGTH: 75
<212> TYPE: PRT
<213> ORGANISM: Homo sapiens

<400> SEQUENCE: 47

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
            20                  25                  30

Asn Phe Leu Asn Leu Pro Glu Val Glu Arg Asp Arg Ile Tyr Gln Asp
        35                  40                  45

```
Glu Arg Glu Arg Ser Met Asn Pro Asn Val Ser Met Val Ser Ser Ala
    50                  55                  60

Ser Ser Ser Pro Ser Ser Ser Arg Thr Pro Gln
65                  70                  75

<210> SEQ ID NO 48
<211> LENGTH: 79
<212> TYPE: PRT
<213> ORGANISM: Homo sapiens

<400> SEQUENCE: 48

Asp Pro Arg Thr Ala Ser Gln Ser Leu Leu Val Asn Leu Arg Ala Met
1               5                   10                  15

Gln Asn Phe Leu Asn Leu Pro Glu Val Glu Arg Asp Arg Ile Tyr Gln
            20                  25                  30

Asp Glu Arg Glu Arg Ser Met Asn Pro Asn Val Ser Met Val Ser Ser
        35                  40                  45

Ala Ser Ser Ser Pro Ser Ser Ser Arg Thr Pro Gln Ala Lys Thr Ser
    50                  55                  60

Thr Pro Thr Thr Asp Leu Pro Ile Lys Val Asp Gly Ala Asn Ile
65                  70                  75

<210> SEQ ID NO 49
<211> LENGTH: 83
<212> TYPE: PRT
<213> ORGANISM: Homo sapiens

<400> SEQUENCE: 49

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
            20                  25                  30

Asn Phe Leu Asn Leu Pro Glu Val Glu Arg Asp Arg Ile Tyr Gln Asp
        35                  40                  45

Glu Arg Glu Arg Ser Met Asn Pro Asn Val Ser Met Val Ser Ser Ala
    50                  55                  60

Ser Ser Ser Pro Ser Ser Ser Arg Thr Pro Gln Ala Lys Thr Ser Thr
65                  70                  75                  80

Pro Thr Thr

<210> SEQ ID NO 50
<211> LENGTH: 85
<212> TYPE: PRT
<213> ORGANISM: Homo sapiens

<400> SEQUENCE: 50

Leu Arg Ala Met Gln Asn Phe Leu Asn Leu Pro Glu Val Glu Arg Asp
1               5                   10                  15

Arg Ile Tyr Gln Asp Glu Arg Glu Arg Ser Met Asn Pro Asn Val Ser
            20                  25                  30

Met Val Ser Ser Ala Ser Ser Ser Pro Ser Ser Ser Arg Thr Pro Gln
        35                  40                  45

Ala Lys Thr Ser Thr Pro Thr Thr Asp Leu Pro Ile Lys Val Asp Gly
    50                  55                  60

Ala Asn Ile Asn Ile Thr Ala Ala Ile Tyr Asp Glu Ile Gln Gln Glu
65                  70                  75                  80

Met Lys Arg Ala Lys
            85
```

```
<210> SEQ ID NO 51
<211> LENGTH: 107
<212> TYPE: PRT
<213> ORGANISM: Homo sapiens

<400> SEQUENCE: 51

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
            20                  25                  30

Asn Phe Leu Asn Leu Pro Glu Val Glu Arg Asp Arg Ile Tyr Gln Asp
        35                  40                  45

Glu Arg Glu Arg Ser Met Asn Pro Asn Val Ser Met Val Ser Ser Ala
    50                  55                  60

Ser Ser Ser Pro Ser Ser Ser Arg Thr Pro Gln Ala Lys Thr Ser Thr
65              70                  75                  80

Pro Thr Thr Asp Leu Pro Ile Lys Val Asp Gly Ala Asn Ile Asn Ile
                85                  90                  95

Thr Ala Ala Ile Tyr Asp Glu Ile Gln Gln Glu
            100                 105

<210> SEQ ID NO 52
<211> LENGTH: 21
<212> TYPE: PRT
<213> ORGANISM: Homo sapiens

<400> SEQUENCE: 52

Thr Gln Gly Leu Leu Ser Glu Ile Leu Arg Lys Glu Glu Asp Pro Arg
1               5                   10                  15

Thr Ala Ser Gln Ser
            20

<210> SEQ ID NO 53
<211> LENGTH: 23
<212> TYPE: PRT
<213> ORGANISM: Homo sapiens

<400> SEQUENCE: 53

Ser Gln Ala Val Phe Ala Arg Val Ala Phe Asn Arg Thr Gln Gly Leu
1               5                   10                  15

Leu Ser Glu Ile Leu Arg Lys
            20

<210> SEQ ID NO 54
<211> LENGTH: 26
<212> TYPE: PRT
<213> ORGANISM: Homo sapiens

<400> SEQUENCE: 54

Val Ser Gln Ala Val Phe Ala Arg Val Ala Phe Asn Arg Thr Gln Gly
1               5                   10                  15

Leu Leu Ser Glu Ile Leu Arg Lys Glu Glu
            20                  25

<210> SEQ ID NO 55
<211> LENGTH: 27
<212> TYPE: PRT
<213> ORGANISM: Homo sapiens

<400> SEQUENCE: 55
```

Ser Gln Ala Val Phe Ala Arg Val Ala Phe Asn Arg Thr Gln Gly Leu
1               5                   10                  15

Leu Ser Glu Ile Leu Arg Lys Glu Glu Asp Pro
            20                  25

<210> SEQ ID NO 56
<211> LENGTH: 28
<212> TYPE: PRT
<213> ORGANISM: Homo sapiens

<400> SEQUENCE: 56

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro
            20                  25

<210> SEQ ID NO 57
<211> LENGTH: 32
<212> TYPE: PRT
<213> ORGANISM: Homo sapiens

<400> SEQUENCE: 57

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro Arg Thr Ala Ser
            20                  25                  30

<210> SEQ ID NO 58
<211> LENGTH: 34
<212> TYPE: PRT
<213> ORGANISM: Homo sapiens

<400> SEQUENCE: 58

Ala Val Phe Ala Arg Val Ala Phe Asn Arg Thr Gln Gly Leu Leu Ser
1               5                   10                  15

Glu Ile Leu Arg Lys Glu Glu Asp Pro Arg Thr Ala Ser Gln Ser Leu
            20                  25                  30

Leu Val

<210> SEQ ID NO 59
<211> LENGTH: 36
<212> TYPE: PRT
<213> ORGANISM: Homo sapiens

<400> SEQUENCE: 59

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
            20                  25                  30

Asn Phe Leu Asn
        35

<210> SEQ ID NO 60
<211> LENGTH: 49
<212> TYPE: PRT
<213> ORGANISM: Homo sapiens

<400> SEQUENCE: 60

Val Ala Phe Asn Arg Thr Gln Gly Leu Leu Ser Glu Ile Leu Arg Lys
1               5                   10                  15

Glu Glu Asp Pro Arg Thr Ala Ser Gln Ser Leu Leu Val Asn Leu Arg
            20                  25                  30

Ala Met Gln Asn Phe Leu Asn Leu Pro Glu Val Glu Arg Asp Arg Ile
           35                  40                  45
Tyr

<210> SEQ ID NO 61
<211> LENGTH: 53
<212> TYPE: PRT
<213> ORGANISM: Homo sapiens

<400> SEQUENCE: 61

Ala Phe Asn Arg Thr Gln Gly Leu Leu Ser Glu Ile Leu Arg Lys Glu
1               5                   10                  15

Glu Asp Pro Arg Thr Ala Ser Gln Ser Leu Leu Val Asn Leu Arg Ala
            20                  25                  30

Met Gln Asn Phe Leu Asn Leu Pro Glu Val Glu Arg Asp Arg Ile Tyr
        35                  40                  45

Gln Asp Glu Arg Glu
    50

<210> SEQ ID NO 62
<211> LENGTH: 54
<212> TYPE: PRT
<213> ORGANISM: Homo sapiens

<400> SEQUENCE: 62

Phe Asn Arg Thr Gln Gly Leu Leu Ser Glu Ile Leu Arg Lys Glu Glu
1               5                   10                  15

Asp Pro Arg Thr Ala Ser Gln Ser Leu Leu Val Asn Leu Arg Ala Met
            20                  25                  30

Gln Asn Phe Leu Asn Leu Pro Glu Val Glu Arg Asp Arg Ile Tyr Gln
        35                  40                  45

Asp Glu Arg Glu Arg Ser
    50

<210> SEQ ID NO 63
<211> LENGTH: 57
<212> TYPE: PRT
<213> ORGANISM: Homo sapiens

<400> SEQUENCE: 63

Ala Val Phe Ala Arg Val Ala Phe Asn Arg Thr Gln Gly Leu Leu Ser
1               5                   10                  15

Glu Ile Leu Arg Lys Glu Glu Asp Pro Arg Thr Ala Ser Gln Ser Leu
            20                  25                  30

Leu Val Asn Leu Arg Ala Met Gln Asn Phe Leu Asn Leu Pro Glu Val
        35                  40                  45

Glu Arg Asp Arg Ile Tyr Gln Asp Glu
    50                  55

<210> SEQ ID NO 64
<211> LENGTH: 60
<212> TYPE: PRT
<213> ORGANISM: Homo sapiens

<400> SEQUENCE: 64

Gly Leu Leu Ser Glu Ile Leu Arg Lys Glu Glu Asp Pro Arg Thr Ala
1               5                   10                  15

Ser Gln Ser Leu Leu Val Asn Leu Arg Ala Met Gln Asn Phe Leu Asn
            20                  25                  30

```
Leu Pro Glu Val Glu Arg Asp Arg Ile Tyr Gln Asp Glu Arg Glu Arg
        35                  40                  45

Ser Met Asn Pro Asn Val Ser Met Val Ser Ser Ala
    50                  55                  60

<210> SEQ ID NO 65
<211> LENGTH: 67
<212> TYPE: PRT
<213> ORGANISM: Homo sapiens

<400> SEQUENCE: 65

Ser Gln Ala Val Phe Ala Arg Val Ala Phe Asn Arg Thr Gln Gly Leu
1               5                   10                  15

Leu Ser Glu Ile Leu Arg Lys Glu Glu Asp Pro Arg Thr Ala Ser Gln
            20                  25                  30

Ser Leu Leu Val Asn Leu Arg Ala Met Gln Asn Phe Leu Asn Leu Pro
        35                  40                  45

Glu Val Glu Arg Asp Arg Ile Tyr Gln Asp Glu Arg Glu Arg Ser Met
    50                  55                  60

Asn Pro Asn
65

<210> SEQ ID NO 66
<211> LENGTH: 69
<212> TYPE: PRT
<213> ORGANISM: Homo sapiens

<400> SEQUENCE: 66

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu
        35                  40                  45

Pro Glu Val Glu Arg Asp Arg Ile Tyr Gln Asp Glu Arg Glu Arg Ser
    50                  55                  60

Met Asn Pro Asn Val
65

<210> SEQ ID NO 67
<211> LENGTH: 69
<212> TYPE: PRT
<213> ORGANISM: Homo sapiens

<400> SEQUENCE: 67

Ser Gln Ala Val Phe Ala Arg Val Ala Phe Asn Arg Thr Gln Gly Leu
1               5                   10                  15

Leu Ser Glu Ile Leu Arg Lys Glu Glu Asp Pro Arg Thr Ala Ser Gln
            20                  25                  30

Ser Leu Leu Val Asn Leu Arg Ala Met Gln Asn Phe Leu Asn Leu Pro
        35                  40                  45

Glu Val Glu Arg Asp Arg Ile Tyr Gln Asp Glu Arg Glu Arg Ser Met
    50                  55                  60

Asn Pro Asn Val Ser
65

<210> SEQ ID NO 68
<211> LENGTH: 72
<212> TYPE: PRT
<213> ORGANISM: Homo sapiens
```

```
<400> SEQUENCE: 68

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
            20                  25                  30

Asn Phe Leu Asn Leu Pro Glu Val Glu Arg Asp Arg Ile Tyr Gln Asp
        35                  40                  45

Glu Arg Glu Arg Ser Met Asn Pro Asn Val Ser Met Val Ser Ser Ala
    50                  55                  60

Ser Ser Ser Pro Ser Ser Arg
65                  70

<210> SEQ ID NO 69
<211> LENGTH: 73
<212> TYPE: PRT
<213> ORGANISM: Homo sapiens

<400> SEQUENCE: 69

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
            20                  25                  30

Asn Phe Leu Asn Leu Pro Glu Val Glu Arg Asp Arg Ile Tyr Gln Asp
        35                  40                  45

Glu Arg Glu Arg Ser Met Asn Pro Asn Val Ser Met Val Ser Ser Ala
    50                  55                  60

Ser Ser Ser Pro Ser Ser Arg Thr
65                  70

<210> SEQ ID NO 70
<211> LENGTH: 75
<212> TYPE: PRT
<213> ORGANISM: Homo sapiens

<400> SEQUENCE: 70

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
            20                  25                  30

Asn Phe Leu Asn Leu Pro Glu Val Glu Arg Asp Arg Ile Tyr Gln Asp
        35                  40                  45

Glu Arg Glu Arg Ser Met Asn Pro Asn Val Ser Met Val Ser Ser Ala
    50                  55                  60

Ser Ser Ser Pro Ser Ser Arg Thr Pro Gln
65                  70                  75

<210> SEQ ID NO 71
<211> LENGTH: 89
<212> TYPE: PRT
<213> ORGANISM: Homo sapiens

<400> SEQUENCE: 71

Ala Phe Asn Arg Thr Gln Gly Leu Leu Ser Glu Ile Leu Arg Lys Glu
1               5                   10                  15

Glu Asp Pro Arg Thr Ala Ser Gln Ser Leu Leu Val Asn Leu Arg Ala
            20                  25                  30

Met Gln Asn Phe Leu Asn Leu Pro Glu Val Glu Arg Asp Arg Ile Tyr
        35                  40                  45
```

Gln Asp Glu Arg Glu Arg Ser Met Asn Pro Asn Val Ser Met Val Ser
    50                  55                  60

Ser Ala Ser Ser Pro Ser Ser Arg Thr Pro Gln Ala Lys Thr
65                  70                  75                  80

Ser Thr Pro Thr Thr Asp Leu Pro Ile
                85

<210> SEQ ID NO 72
<211> LENGTH: 92
<212> TYPE: PRT
<213> ORGANISM: Homo sapiens

<400> SEQUENCE: 72

Ala Val Phe Ala Arg Val Ala Phe Asn Arg Thr Gln Gly Leu Leu Ser
1               5                   10                  15

Glu Ile Leu Arg Lys Glu Glu Asp Pro Arg Thr Ala Ser Gln Ser Leu
            20                  25                  30

Leu Val Asn Leu Arg Ala Met Gln Asn Phe Leu Asn Leu Pro Glu Val
        35                  40                  45

Glu Arg Asp Arg Ile Tyr Gln Asp Glu Arg Glu Arg Ser Met Asn Pro
    50                  55                  60

Asn Val Ser Met Val Ser Ser Ala Ser Ser Pro Ser Ser Ser Arg
65                  70                  75                  80

Thr Pro Gln Ala Lys Thr Ser Thr Pro Thr Thr Asp
                85                  90

<210> SEQ ID NO 73
<211> LENGTH: 100
<212> TYPE: PRT
<213> ORGANISM: Homo sapiens

<400> SEQUENCE: 73

Ala Val Phe Ala Arg Val Ala Phe Asn Arg Thr Gln Gly Leu Leu Ser
1               5                   10                  15

Glu Ile Leu Arg Lys Glu Glu Asp Pro Arg Thr Ala Ser Gln Ser Leu
            20                  25                  30

Leu Val Asn Leu Arg Ala Met Gln Asn Phe Leu Asn Leu Pro Glu Val
        35                  40                  45

Glu Arg Asp Arg Ile Tyr Gln Asp Glu Arg Glu Arg Ser Met Asn Pro
    50                  55                  60

Asn Val Ser Met Val Ser Ser Ala Ser Ser Pro Ser Ser Ser Arg
65                  70                  75                  80

Thr Pro Gln Ala Lys Thr Ser Thr Pro Thr Thr Asp Leu Pro Ile Lys
                85                  90                  95

Val Asp Gly Ala
            100

<210> SEQ ID NO 74
<211> LENGTH: 103
<212> TYPE: PRT
<213> ORGANISM: Homo sapiens

<400> SEQUENCE: 74

Ala Val Phe Ala Arg Val Ala Phe Asn Arg Thr Gln Gly Leu Leu Ser
1               5                   10                  15

Glu Ile Leu Arg Lys Glu Glu Asp Pro Arg Thr Ala Ser Gln Ser Leu
            20                  25                  30

Leu Val Asn Leu Arg Ala Met Gln Asn Phe Leu Asn Leu Pro Glu Val

-continued

```
                35                  40                  45
Glu Arg Asp Arg Ile Tyr Gln Asp Glu Arg Glu Arg Ser Met Asn Pro
 50                  55                  60

Asn Val Ser Met Val Ser Ser Ala Ser Ser Pro Ser Ser Ser Arg
 65                  70                  75                  80

Thr Pro Gln Ala Lys Thr Ser Thr Pro Thr Thr Asp Leu Pro Ile Lys
                 85                  90                  95

Val Asp Gly Ala Asn Ile Asn
            100

<210> SEQ ID NO 75
<211> LENGTH: 107
<212> TYPE: PRT
<213> ORGANISM: Homo sapiens

<400> SEQUENCE: 75

Val Ser Gln Ala Val Phe Ala Arg Val Ala Phe Asn Arg Thr Gln Gly
 1               5                  10                  15

Leu Leu Ser Glu Ile Leu Arg Lys Glu Glu Asp Pro Arg Thr Ala Ser
                20                  25                  30

Gln Ser Leu Leu Val Asn Leu Arg Ala Met Gln Asn Phe Leu Asn Leu
            35                  40                  45

Pro Glu Val Glu Arg Asp Arg Ile Tyr Gln Asp Glu Arg Glu Arg Ser
         50                  55                  60

Met Asn Pro Asn Val Ser Met Val Ser Ser Ala Ser Ser Pro Ser
 65                  70                  75                  80

Ser Ser Arg Thr Pro Gln Ala Lys Thr Ser Thr Pro Thr Thr Asp Leu
                85                  90                  95

Pro Ile Lys Val Asp Gly Ala Asn Ile Asn Ile
            100                 105

<210> SEQ ID NO 76
<211> LENGTH: 116
<212> TYPE: PRT
<213> ORGANISM: Homo sapiens

<400> SEQUENCE: 76

Ser Gln Ala Val Phe Ala Arg Val Ala Phe Asn Arg Thr Gln Gly Leu
 1               5                  10                  15

Leu Ser Glu Ile Leu Arg Lys Glu Glu Asp Pro Arg Thr Ala Ser Gln
                20                  25                  30

Ser Leu Leu Val Asn Leu Arg Ala Met Gln Asn Phe Leu Asn Leu Pro
            35                  40                  45

Glu Val Glu Arg Asp Arg Ile Tyr Gln Asp Glu Arg Glu Arg Ser Met
         50                  55                  60

Asn Pro Asn Val Ser Met Val Ser Ser Ala Ser Ser Ser Pro Ser Ser
 65                  70                  75                  80

Ser Arg Thr Pro Gln Ala Lys Thr Ser Thr Pro Thr Thr Asp Leu Pro
                85                  90                  95

Ile Lys Val Asp Gly Ala Asn Ile Asn Ile Thr Ala Ala Ile Tyr Asp
            100                 105                 110

Glu Ile Gln Gln
        115

<210> SEQ ID NO 77
<211> LENGTH: 114
<212> TYPE: PRT
<213> ORGANISM: Homo sapiens
```

```
<400> SEQUENCE: 77

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu
        35                  40                  45

Pro Glu Val Glu Arg Asp Arg Ile Tyr Gln Asp Glu Arg Glu Arg Ser
    50                  55                  60

Met Asn Pro Asn Val Ser Met Val Ser Ser Ala Ser Ser Ser Pro Ser
65                  70                  75                  80

Ser Ser Arg Thr Pro Gln Ala Lys Thr Ser Thr Pro Thr Thr Asp Leu
            85                  90                  95

Pro Ile Lys Val Asp Gly Ala Asn Ile Asn Ile Thr Ala Ala Ile Tyr
        100                 105                 110

Asp Glu

<210> SEQ ID NO 78
<211> LENGTH: 21
<212> TYPE: PRT
<213> ORGANISM: Homo sapiens

<400> SEQUENCE: 78

Val Phe Ala Arg Val Ala Phe Asn Arg Thr Gln Gly Leu Leu Ser Glu
1               5                   10                  15

Ile Leu Arg Lys Glu
            20

<210> SEQ ID NO 79
<211> LENGTH: 22
<212> TYPE: PRT
<213> ORGANISM: Homo sapiens

<400> SEQUENCE: 79

Ala Val Phe Ala Arg Val Ala Phe Asn Arg Thr Gln Gly Leu Leu Ser
1               5                   10                  15

Glu Ile Leu Arg Lys Glu
            20

<210> SEQ ID NO 80
<211> LENGTH: 25
<212> TYPE: PRT
<213> ORGANISM: Homo sapiens

<400> SEQUENCE: 80

Val Ser Gln Ala Val Phe Ala Arg Val Ala Phe Asn Arg Thr Gln Gly
1               5                   10                  15

Leu Leu Ser Glu Ile Leu Arg Lys Glu
            20                  25

<210> SEQ ID NO 81
<211> LENGTH: 35
<212> TYPE: PRT
<213> ORGANISM: Homo sapiens

<400> SEQUENCE: 81

Phe Asn Arg Thr Gln Gly Leu Leu Ser Glu Ile Leu Arg Lys Glu Glu
1               5                   10                  15

Asp Pro Arg Thr Ala Ser Gln Ser Leu Leu Val Asn Leu Arg Ala Met
```

```
                    20                  25                  30

Gln Asn Phe
        35

<210> SEQ ID NO 82
<211> LENGTH: 35
<212> TYPE: PRT
<213> ORGANISM: Homo sapiens

<400> SEQUENCE: 82

Phe Asn Arg Thr Gln Gly Leu Leu Ser Glu Ile Leu Arg Lys Glu Glu
1               5                   10                  15

Asp Pro Arg Thr Ala Ser Gln Ser Leu Leu Val Asn Leu Arg Ala Met
                20                  25                  30

Gln Asn Phe
        35

<210> SEQ ID NO 83
<211> LENGTH: 49
<212> TYPE: PRT
<213> ORGANISM: Homo sapiens

<400> SEQUENCE: 83

Gln Gly Leu Leu Ser Glu Ile Leu Arg Lys Glu Glu Asp Pro Arg Thr
1               5                   10                  15

Ala Ser Gln Ser Leu Leu Val Asn Leu Arg Ala Met Gln Asn Phe Leu
                20                  25                  30

Asn Leu Pro Glu Val Glu Arg Asp Arg Ile Tyr Gln Asp Glu Arg Glu
            35                  40                  45

Arg

<210> SEQ ID NO 84
<211> LENGTH: 55
<212> TYPE: PRT
<213> ORGANISM: Homo sapiens

<400> SEQUENCE: 84

Arg Val Ala Phe Asn Arg Thr Gln Gly Leu Leu Ser Glu Ile Leu Arg
1               5                   10                  15

Lys Glu Glu Asp Pro Arg Thr Ala Ser Gln Ser Leu Leu Val Asn Leu
                20                  25                  30

Arg Ala Met Gln Asn Phe Leu Asn Leu Pro Glu Val Glu Arg Asp Arg
            35                  40                  45

Ile Tyr Gln Asp Glu Arg Glu
        50                  55

<210> SEQ ID NO 85
<211> LENGTH: 56
<212> TYPE: PRT
<213> ORGANISM: Homo sapiens

<400> SEQUENCE: 85

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
                20                  25                  30

Asn Phe Leu Asn Leu Pro Glu Val Glu Arg Asp Arg Ile Tyr Gln Asp
            35                  40                  45

Glu Arg Glu Arg Ser Met Asn Pro
        50                  55
```

<210> SEQ ID NO 86
<211> LENGTH: 75
<212> TYPE: PRT
<213> ORGANISM: Homo sapiens

<400> SEQUENCE: 86

Asn Arg Thr Gln Gly Leu Leu Ser Glu Ile Leu Arg Lys Glu Glu Asp
1               5                   10                  15

Pro Arg Thr Ala Ser Gln Ser Leu Leu Val Asn Leu Arg Ala Met Gln
            20                  25                  30

Asn Phe Leu Asn Leu Pro Glu Val Glu Arg Asp Arg Ile Tyr Gln Asp
        35                  40                  45

Glu Arg Glu Arg Ser Met Asn Pro Asn Val Ser Met Val Ser Ser Ala
    50                  55                  60

Ser Ser Ser Pro Ser Ser Arg Thr Pro Gln
65                  70                  75

<210> SEQ ID NO 87
<211> LENGTH: 12
<212> TYPE: PRT
<213> ORGANISM: Homo sapiens

<400> SEQUENCE: 87

Lys Thr Ser Thr Pro Thr Thr Asp Leu Pro Ile Lys
1               5                   10

<210> SEQ ID NO 88
<211> LENGTH: 25
<212> TYPE: PRT
<213> ORGANISM: Homo sapiens

<400> SEQUENCE: 88

Ala Ser Ser Ser Pro Ser Ser Arg Thr Pro Gln Ala Lys Thr Ser
1               5                   10                  15

Thr Pro Thr Thr Asp Leu Pro Ile Lys
            20                  25

<210> SEQ ID NO 89
<211> LENGTH: 25
<212> TYPE: PRT
<213> ORGANISM: Homo sapiens

<400> SEQUENCE: 89

Thr Pro Gln Ala Lys Thr Ser Thr Pro Thr Thr Asp Leu Pro Ile Lys
1               5                   10                  15

Val Asp Gly Ala Asn Ile Asn Ile Thr
            20                  25

<210> SEQ ID NO 90
<211> LENGTH: 26
<212> TYPE: PRT
<213> ORGANISM: Homo sapiens

<400> SEQUENCE: 90

Lys Thr Ser Thr Pro Thr Thr Asp Leu Pro Ile Lys Val Asp Gly Ala
1               5                   10                  15

Asn Ile Asn Ile Thr Ala Ala Ile Tyr Asp
            20                  25

<210> SEQ ID NO 91
<211> LENGTH: 26

<212> TYPE: PRT
<213> ORGANISM: Homo sapiens

<400> SEQUENCE: 91

Ser Ala Ser Ser Ser Pro Ser Ser Arg Thr Pro Gln Ala Lys Thr
1               5                   10                  15

Ser Thr Pro Thr Thr Asp Leu Pro Ile Lys
                20                  25

<210> SEQ ID NO 92
<211> LENGTH: 30
<212> TYPE: PRT
<213> ORGANISM: Homo sapiens

<400> SEQUENCE: 92

Ser Pro Ser Ser Ser Arg Thr Pro Gln Ala Lys Thr Ser Thr Pro Thr
1               5                   10                  15

Thr Asp Leu Pro Ile Lys Val Asp Gly Ala Asn Ile Asn Ile
                20                  25                  30

<210> SEQ ID NO 93
<211> LENGTH: 31
<212> TYPE: PRT
<213> ORGANISM: Homo sapiens

<400> SEQUENCE: 93

Gln Ala Lys Thr Ser Thr Pro Thr Thr Asp Leu Pro Ile Lys Val Asp
1               5                   10                  15

Gly Ala Asn Ile Asn Ile Thr Ala Ala Ile Tyr Asp Glu Ile Gln
                20                  25                  30

<210> SEQ ID NO 94
<211> LENGTH: 32
<212> TYPE: PRT
<213> ORGANISM: Homo sapiens

<400> SEQUENCE: 94

Ser Ser Ser Arg Thr Pro Gln Ala Lys Thr Ser Thr Pro Thr Thr Asp
1               5                   10                  15

Leu Pro Ile Lys Val Asp Gly Ala Asn Ile Asn Ile Thr Ala Ala Ile
                20                  25                  30

<210> SEQ ID NO 95
<211> LENGTH: 34
<212> TYPE: PRT
<213> ORGANISM: Homo sapiens

<400> SEQUENCE: 95

Ser Ala Ser Ser Ser Pro Ser Ser Arg Thr Pro Gln Ala Lys Thr
1               5                   10                  15

Ser Thr Pro Thr Thr Asp Leu Pro Ile Lys Val Asp Gly Ala Asn Ile
                20                  25                  30

Asn Ile

<210> SEQ ID NO 96
<211> LENGTH: 36
<212> TYPE: PRT
<213> ORGANISM: Homo sapiens

<400> SEQUENCE: 96

Ala Ser Ser Ser Pro Ser Ser Arg Thr Pro Gln Ala Lys Thr Ser
1               5                   10                  15

Thr Pro Thr Thr Asp Leu Pro Ile Lys Val Asp Gly Ala Asn Ile Asn
            20                  25                  30

Ile Thr Ala Ala
            35

<210> SEQ ID NO 97
<211> LENGTH: 43
<212> TYPE: PRT
<213> ORGANISM: Homo sapiens

<400> SEQUENCE: 97

Met Val Ser Ser Ala Ser Ser Pro Ser Ser Arg Thr Pro Gln
1               5                   10                  15

Ala Lys Thr Ser Thr Pro Thr Thr Asp Leu Pro Ile Lys Val Asp Gly
            20                  25                  30

Ala Asn Ile Asn Ile Thr Ala Ala Ile Tyr Asp
            35                  40

<210> SEQ ID NO 98
<211> LENGTH: 44
<212> TYPE: PRT
<213> ORGANISM: Homo sapiens

<400> SEQUENCE: 98

Ser Ser Pro Ser Ser Ser Arg Thr Pro Gln Ala Lys Thr Ser Thr Pro
1               5                   10                  15

Thr Thr Asp Leu Pro Ile Lys Val Asp Gly Ala Asn Ile Asn Ile Thr
            20                  25                  30

Ala Ala Ile Tyr Asp Glu Ile Gln Gln Glu Met Lys
            35                  40

<210> SEQ ID NO 99
<211> LENGTH: 45
<212> TYPE: PRT
<213> ORGANISM: Homo sapiens

<400> SEQUENCE: 99

Ile Tyr Gln Asp Glu Arg Glu Arg Ser Met Asn Pro Asn Val Ser Met
1               5                   10                  15

Val Ser Ser Ala Ser Ser Ser Pro Ser Ser Arg Thr Pro Gln Ala
            20                  25                  30

Lys Thr Ser Thr Pro Thr Thr Asp Leu Pro Ile Lys Val
            35                  40                  45

<210> SEQ ID NO 100
<211> LENGTH: 48
<212> TYPE: PRT
<213> ORGANISM: Homo sapiens

<400> SEQUENCE: 100

Val Ser Met Val Ser Ser Ala Ser Ser Pro Ser Ser Arg Thr
1               5                   10                  15

Pro Gln Ala Lys Thr Ser Thr Pro Thr Thr Asp Leu Pro Ile Lys Val
            20                  25                  30

Asp Gly Ala Asn Ile Asn Ile Thr Ala Ala Ile Tyr Asp Glu Ile Gln
            35                  40                  45

<210> SEQ ID NO 101
<211> LENGTH: 45
<212> TYPE: PRT
<213> ORGANISM: Homo sapiens

```
<400> SEQUENCE: 101

Ser Met Asn Pro Asn Val Ser Met Val Ser Ala Ser Ser Ser Pro
1               5                   10                  15

Ser Ser Ser Arg Thr Pro Gln Ala Lys Thr Ser Thr Pro Thr Asp
                20                  25                  30

Leu Pro Ile Lys Val Asp Gly Ala Asn Ile Asn Ile Thr
            35                  40                  45

<210> SEQ ID NO 102
<211> LENGTH: 47
<212> TYPE: PRT
<213> ORGANISM: Homo sapiens

<400> SEQUENCE: 102

Ser Ala Ser Ser Ser Pro Ser Ser Arg Thr Pro Gln Ala Lys Thr
1               5                   10                  15

Ser Thr Pro Thr Thr Asp Leu Pro Ile Lys Val Asp Gly Ala Asn Ile
                20                  25                  30

Asn Ile Thr Ala Ala Ile Tyr Asp Glu Ile Gln Gln Glu Met Lys
            35                  40                  45

<210> SEQ ID NO 103
<211> LENGTH: 49
<212> TYPE: PRT
<213> ORGANISM: Homo sapiens

<400> SEQUENCE: 103

Val Glu Arg Asp Arg Ile Tyr Gln Asp Glu Arg Glu Arg Ser Met Asn
1               5                   10                  15

Pro Asn Val Ser Met Val Ser Ser Ala Ser Ser Ser Pro Ser Ser Ser
                20                  25                  30

Arg Thr Pro Gln Ala Lys Thr Ser Thr Pro Thr Thr Asp Leu Pro Ile
            35                  40                  45

Lys

<210> SEQ ID NO 104
<211> LENGTH: 51
<212> TYPE: PRT
<213> ORGANISM: Homo sapiens

<400> SEQUENCE: 104

Val Ser Ser Ala Ser Ser Ser Pro Ser Ser Arg Thr Pro Gln Ala
1               5                   10                  15

Lys Thr Ser Thr Pro Thr Thr Asp Leu Pro Ile Lys Val Asp Gly Ala
                20                  25                  30

Asn Ile Asn Ile Thr Ala Ala Ile Tyr Asp Glu Ile Gln Gln Glu Met
            35                  40                  45

Lys Arg Ala
        50

<210> SEQ ID NO 105
<211> LENGTH: 24
<212> TYPE: PRT
<213> ORGANISM: Homo sapiens

<400> SEQUENCE: 105

Val Ser Ser Ala Ser Ser Ser Pro Ser Ser Arg Thr Pro Gln Ala
1               5                   10                  15

Lys Thr Ser Thr Pro Thr Thr Asp
                20
```

<210> SEQ ID NO 106
<211> LENGTH: 12
<212> TYPE: PRT
<213> ORGANISM: Homo sapiens

<400> SEQUENCE: 106

Pro Ile Lys Val Asp Gly Ala Asn Ile Asn Ile Thr
1               5                   10

<210> SEQ ID NO 107
<211> LENGTH: 29
<212> TYPE: PRT
<213> ORGANISM: Homo sapiens

<400> SEQUENCE: 107

Thr Thr Asp Leu Pro Ile Lys Val Asp Gly Ala Asn Ile Asn Ile Thr
1               5                   10                  15

Ala Ala Ile Tyr Asp Glu Ile Gln Gln Glu Met Lys Arg
            20                  25

<210> SEQ ID NO 108
<211> LENGTH: 22
<212> TYPE: PRT
<213> ORGANISM: Homo sapiens

<400> SEQUENCE: 108

Thr Thr Asp Leu Pro Ile Lys Val Asp Gly Ala Asn Ile Asn Ile Thr
1               5                   10                  15

Ala Ala Ile Tyr Asp Glu
            20

<210> SEQ ID NO 109
<211> LENGTH: 24
<212> TYPE: PRT
<213> ORGANISM: Homo sapiens

<400> SEQUENCE: 109

Pro Ile Lys Val Asp Gly Ala Asn Ile Asn Ile Thr Ala Ala Ile Tyr
1               5                   10                  15

Asp Glu Ile Gln Gln Glu Met Lys
            20

<210> SEQ ID NO 110
<211> LENGTH: 14
<212> TYPE: PRT
<213> ORGANISM: Homo sapiens

<400> SEQUENCE: 110

Asp Leu Pro Ile Lys Val Asp Gly Ala Asn Ile Asn Ile Thr
1               5                   10

<210> SEQ ID NO 111
<211> LENGTH: 123
<212> TYPE: PRT
<213> ORGANISM: Homo sapiens

<400> SEQUENCE: 111

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu

-continued

```
                35                  40                  45
Pro Glu Val Glu Arg Asp Arg Ile Tyr Gln Asp Glu Arg Glu Arg Ser
    50                  55                  60

Met Asn Pro Asn Val Ser Met Val Ser Ser Ala Ser Ser Ser Pro Ser
65                  70                  75                  80

Ser Ser Arg Thr Pro Gln Ala Lys Thr Ser Thr Pro Thr Thr Asp Leu
                85                  90                  95

Pro Ile Lys Val Asp Gly Ala Asn Ile Asn Ile Thr Ala Ala Ile Tyr
                100                 105                 110

Asp Glu Ile Gln Gln Glu Met Lys Arg Ala Lys
                115                 120

<210> SEQ ID NO 112
<211> LENGTH: 19
<212> TYPE: DNA
<213> ORGANISM: Artificial Sequence
<220> FEATURE:
<223> OTHER INFORMATION: Synthetic primer

<400> SEQUENCE: 112
gtgtcccaag ctgtctttg                                            19

<210> SEQ ID NO 113
<211> LENGTH: 19
<212> TYPE: DNA
<213> ORGANISM: Artificial Sequence
<220> FEATURE:
<223> OTHER INFORMATION: Synthetic primer

<400> SEQUENCE: 113
cttggccctt ttcatctcc                                            19
```